United States Patent
Lee et al.

(10) Patent No.: US 9,988,678 B2
(45) Date of Patent: Jun. 5, 2018

(54) DNA SEQUENCING DETECTION FIELD EFFECT TRANSISTOR

(71) Applicant: International Business Machines Corporation, Armonk, NY (US)

(72) Inventors: Sanghoon Lee, White Plains, NY (US); Effendi Leobandung, Stormville, NY (US); Renee T. Mo, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 94 days.

(21) Appl. No.: 14/923,091

(22) Filed: Oct. 26, 2015

(65) Prior Publication Data

US 2017/0114402 A1    Apr. 27, 2017

(51) Int. Cl.
  *C12Q 1/68* (2018.01)
  *G01N 27/414* (2006.01)

(52) U.S. Cl.
  CPC ....... *C12Q 1/6869* (2013.01); *G01N 27/4145* (2013.01)

(58) Field of Classification Search
  CPC .......................... C12Q 1/6869; G01N 27/4145
  See application file for complete search history.

(56) References Cited

U.S. PATENT DOCUMENTS

| 8,664,700 | B2 | 3/2014 | Lee et al. |
| 8,878,258 | B2 | 11/2014 | Monfray et al. |
| 8,936,763 | B2 | 1/2015 | Rothberg et al. |

(Continued)

FOREIGN PATENT DOCUMENTS

| GB | 2508582 A | 6/2014 |
| WO | 2014/207877 A1 | 12/2014 |

OTHER PUBLICATIONS

Sakata, T., et al., "DNA Sequencing Using Genetic Field Effect Transistor", Transducers '05, 13th International Conference on Solid-State Sensors, Actuators and Microsystems, Jun. 5-9, 2005, Seoul, Korea, pp. 1676-1679.

(Continued)

*Primary Examiner* — Robert Carpenter
(74) *Attorney, Agent, or Firm* — Scully, Scott, Murphy & Presser, P.C.; Louis J. Percello, Esq.

(57) ABSTRACT

A semiconductor structure is provided that can be used for DNA sequencing detection. The semiconductor structure includes a doped epitaxial source semiconductor material structure located on a first portion of a semiconductor substrate and a doped epitaxial drain semiconductor material structure located on a second portion of the semiconductor substrate. A gate dielectric portion is located on a third portion of the semiconductor substrate and positioned between the doped epitaxial source semiconductor material structure and the doped epitaxial drain semiconductor material structure. A non-stick nucleotide, DNA and DNA polymerase material structure is located atop the doped epitaxial source semiconductor material structure and atop the doped epitaxial drain semiconductor material structure, wherein a cavity is present in the non-stick nucleotide, DNA and DNA polymerase material structure that exposes a topmost surface of the gate dielectric portion.

18 Claims, 31 Drawing Sheets

(56) References Cited

U.S. PATENT DOCUMENTS

| | | | |
|---|---|---|---|
| 2012/0021918 A1* | 1/2012 | Bashir | B82Y 15/00 506/2 |
| 2013/0270521 A1 | 10/2013 | Peng et al. | |
| 2013/0271150 A1 | 10/2013 | Peng et al. | |
| 2015/0014752 A1 | 1/2015 | D'Emic et al. | |

OTHER PUBLICATIONS

Eid, J., et al., "Real-Time DNA Sequencing from Single Polymerase Molecules", Science, Jan. 2009, pp. 133-138, vol. 323.

* cited by examiner

DNA SEQUENCING DETECTION FIELD EFFECT TRANSISTOR

BACKGROUND

The present application relates to semiconductor technology, and more particularly to a field effect transistor (FET) that can be used for DNA sequencing detection.

DNA sequencing is the process of determining the precise order of nucleotides within a DNA molecule. DNA sequencing includes any method or technology that is used to determine the order of the four bases—adenine, guanine, cytosine, and thymine—in a strand of DNA. The advent of rapid DNA sequencing methods has greatly accelerated biological and medical research and discovery.

Knowledge of DNA sequences has become indispensable for basic biological research, and in numerous applied fields such as medical diagnosis, biotechnology, forensic biology, virology and biological systematics. The rapid speed of sequencing attained with modern DNA sequencing technology has been instrumental in the sequencing of complete DNA sequences, or genomes of numerous types and species of life, including the human genome and other complete DNA sequences of many animal, plant, and microbial species.

DNA sequencing methods currently under development include reading the sequence as a DNA strand transmitted through nanopores, and microscopy-based techniques, such as atomic force microscopy or transmission electron microscopy that are used to identify the positions of individual nucleotides within long DNA fragments (>5,000 bp) by nucleotide labeling with heavier elements (e.g., halogens) for visual detection and recording.

Future generation technologies aim to increase throughput and decrease the time and cost by eliminating the need for excessive reagents and harnessing the processivity of DNA polymerase. Notably, and in order to achieve low-cost and rapid DNA sequencing for genomes with large-scale complexity, it is necessary to increase the speed and length of individual sequencing reads. Moreover, a high level multiplex of such sequencing processes will eventually become essential to improve overall throughput.

In view of the above, there is a need for providing a DNA sequencing detection method which overcomes the drawbacks associated with prior art DNA sequencing detection methods.

SUMMARY

In one aspect of the present application, a semiconductor structure is provided that can be used for DNA sequencing detection. In one embodiment of the present application, the semiconductor structure includes a doped epitaxial source semiconductor material structure located on a first portion of a semiconductor substrate and a doped epitaxial drain semiconductor material structure located on a second portion of the semiconductor substrate. A gate dielectric portion is located on a third portion of the semiconductor substrate and positioned between the doped epitaxial source semiconductor material structure and the doped epitaxial drain semiconductor material structure. A non-stick nucleotide, DNA and DNA polymerase material structure is located atop the doped epitaxial source semiconductor material structure and atop the doped epitaxial drain semiconductor material structure, wherein a cavity is present in the non-stick nucleotide, DNA and DNA polymerase material structure that exposes a topmost surface of the gate dielectric portion.

In yet another aspect of the present application, a method of DNA sequencing detection is provided. In one embodiment of the present application, the method includes providing a semiconductor structure that includes a doped epitaxial source semiconductor material structure located on a first portion of a semiconductor substrate and a doped epitaxial drain semiconductor material structure located on a second portion of the semiconductor substrate; a gate dielectric portion located on a third portion of the semiconductor substrate and positioned between the doped epitaxial source semiconductor material structure and the doped epitaxial drain semiconductor material structure; and a non-stick nucleotide, DNA and DNA polymerase material structure located atop the doped epitaxial source semiconductor material structure and atop the doped epitaxial drain semiconductor material structure, wherein a cavity is present in the non-stick nucleotide, DNA and DNA polymerase material structure that exposes a topmost surface of the gate dielectric portion. Next, a DNA polymerase is formed on a portion of the topmost surface of the gate dielectric portion and within the cavity. A DNA template is then attached to a surface of the DNA polymerase, wherein the DNA template is present in a solution that further contains various nucleotides. Next, a change in threshold voltage caused by each nucleotide present in the solution is measured by monitoring the change of drain current of the semiconductor structure.

DETAILED DESCRIPTION

Figure 1A:
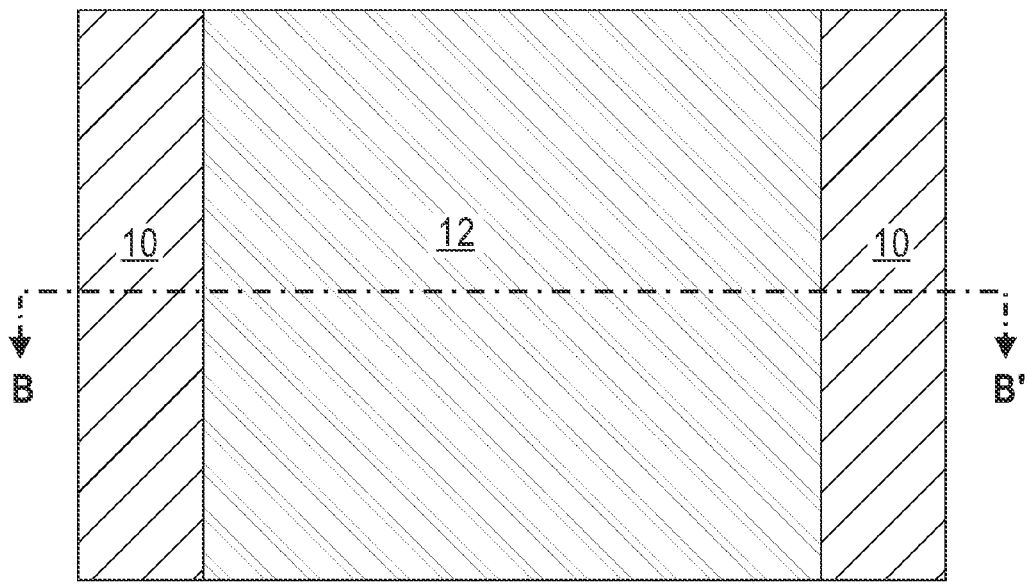
FIG. 1A is a top down view of an exemplary semiconductor structure of the present application including a semiconductor substrate having a mesa region that is capped with a hard mask portion, the mesa region is surrounded by a trench opening.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

It will be understood that when an element as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "beneath" or "under" another element, it can be directly beneath or under the other element, or intervening elements may be present. In contrast, when an element is referred to as being "directly beneath" or "directly under" another element, there are no intervening elements present.

Figure 1B:
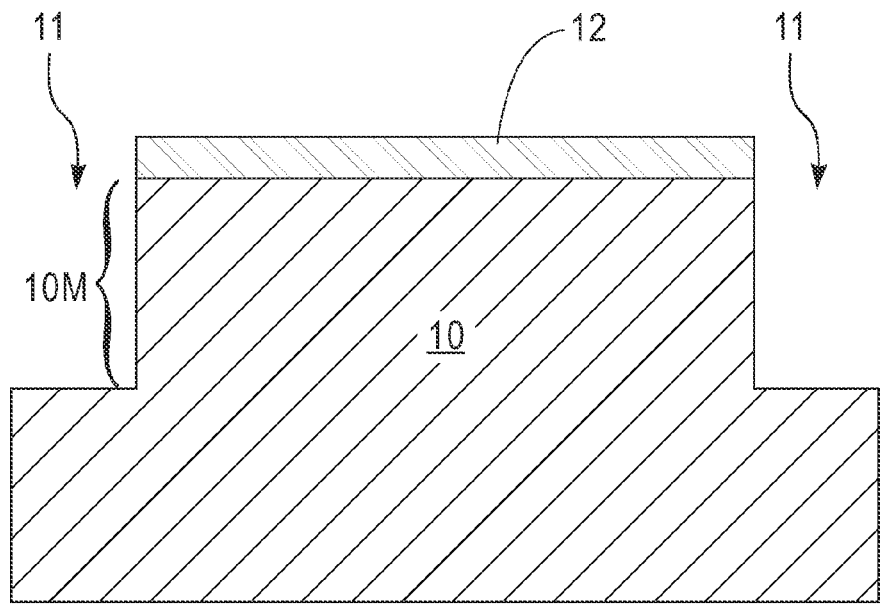
FIG. 1B is a cross sectional view of the exemplary semiconductor structure of FIG. 1A through vertical plane B-B'.

Referring first to FIGS. 1A-1B, there are illustrated various views of an exemplary semiconductor structure of the present application including a semiconductor substrate 10 having a mesa region 10M that is capped with a hard mask portion 12 and is surrounded by a trench opening 11.

The exemplary semiconductor structure of FIGS. 1A-1B can be provided by first providing a semiconductor substrate 10. In one embodiment of the present application, the semiconductor substrate 10 is a bulk semiconductor substrate. By "bulk semiconductor substrate" it is meant that the entire substrate is composed of at least one semiconductor material. Exemplary semiconductor materials that can provide at least a portion of the bulk semiconductor substrate include, for example, Si, Ge, SiGe, SiC, SiGeC, III-V compound semiconductors or II-VI compound semiconductors. Typically, the semiconductor material that provides the bulk semiconductor substrate that can be employed as semiconductor substrate 10 is a single crystalline semiconductor material. In one example, the semiconductor substrate 10 is single crystalline silicon.

In some embodiments of the present application (not shown), the semiconductor substrate 10 may include a semiconductor-on-insulator (SOI) substrate. The SOI substrate includes, from bottom to top, a handle substrate, an insulator layer and a topmost semiconductor layer. In such an embodiment, the top semiconductor layer could be patterned to form the mesa region 10M of the semiconductor substrate. The handle substrate provides mechanical support for the buried insulator layer and the topmost semiconductor layer.

The handle substrate and the topmost semiconductor layer of the SOI substrate may comprise the same, or different, semiconductor material. The semiconductor material of the handle substrate and the topmost semiconductor layer may include one of the semiconductor materials mentioned above for the bulk semiconductor substrate. Multilayers of semiconductor materials can also be used as the semiconductor material of the handle substrate and the topmost semiconductor layer. In one embodiment, the handle substrate and the topmost semiconductor layer are both comprised of silicon. In some embodiments, the handle substrate is a non-semiconductor material including, for example, a dielectric material and/or a conductive material. In yet other embodiments, the handle substrate can be omitted and a substrate including an insulator layer and a topmost semiconductor layer can be used as semiconductor substrate 10.

In some embodiments, the handle substrate and the topmost semiconductor layer may have the same or different crystal orientation. For example, the crystal orientation of the handle substrate and/or the topmost semiconductor layer may be {100}, {110}, or {111}. Other crystallographic orientations besides those specifically mentioned can also be used in the present application. The handle substrate and/or the topmost semiconductor layer of the SOI substrate may be a single crystalline semiconductor material, a polycrystalline material, or an amorphous material. Typically, at least the topmost semiconductor layer is a single crystalline semiconductor material. In some embodiments, the topmost semiconductor layer that is located atop the buried insulator layer can be processed to include semiconductor regions having different crystal orientations.

The insulator layer of the SOI substrate may be a crystalline or non-crystalline oxide or nitride. In one embodiment, the buried insulator layer is an oxide such as, for example, silicon dioxide. In some embodiments, the insulator layer is continuously presented between the topmost semiconductor layer and the handle substrate.

The SOI substrate may be formed utilizing standard processes including for example, SIMOX (separation by ion implantation of oxygen) or layer transfer. When a layer transfer process is employed, an optional thinning step may follow the bonding of two semiconductor wafers together. The optional thinning step reduces the thickness of the semiconductor layer to a layer having a thickness that is more desirable.

In some embodiments of the present application, the semiconductor substrate 10 is entirely or at least partially (i.e., an uppermost or topmost semiconductor surface) doped with an n-type or p-type dopant. The term "p-type" refers to the addition of impurities to an intrinsic semiconductor that creates deficiencies of valence electrons. In a silicon-containing semiconductor material, examples of p-type dopants, i.e., impurities, include, but are not limited to, boron, aluminum, gallium and indium. "N-type" refers to the addition of impurities that contributes free electrons to an intrinsic semiconductor. In a silicon containing semiconductor material, examples of n-type dopants, i.e., impurities, include, but are not limited to, antimony, arsenic and phosphorous. In one embodiment of the present application and depending upon a target threshold voltage, the concentration of dopant that can be present within semiconductor substrate 10 can be within a range from $10^{16}$ atoms/cm$^3$ to $10^{19}$ atoms/cm$^3$.

Next, a hard mask layer (not shown) is formed continuously (without any breaks or interruptions) on a topmost surface of the semiconductor substrate 10. The hard mask layer may comprise any hard mask material such as, for example, silicon dioxide, silicon nitride, and/or silicon oxynitride. In one embodiment, the hard mask layer is composed of silicon nitride.

The hard mask material that provides the hard mask layer can be formed utilizing a conventional deposition process such as, for example, chemical vapor deposition or plasma enhanced chemical vapor deposition. The hard mask material that provides the hard mask layer can have a thickness from 20 nm to 100 nm. Other thicknesses that are lesser than, or greater than, the aforementioned thickness range can also be employed as the thickness of the hard mask material that provides the hard mask layer.

After providing the hard mask layer, the hard mask layer is then patterned to provide a hard mask portion 12. The patterning of the hard mask layer may be performed by lithography and etching. Lithography includes forming a photoresist material (not shown) atop a material or material stack to be patterned; in the present application the photoresist material is formed atop the hard mask layer. The photoresist material may include a positive-tone photoresist composition, a negative-tone photoresist composition or a hybrid-tone photoresist composition. The photoresist material may be formed by a deposition process such as, for example, spin-on coating. After forming the photoresist material, the deposited photoresist material is subjected to a pattern of irradiation. Next, the exposed photoresist material is developed utilizing a conventional resist developer. This provides a patterned photoresist atop a portion of the hard mask layer. The pattern provided by the patterned photoresist is thereafter transferred into the underlying material layer or material layers utilizing at least one pattern transfer etching process. Typically, the at least one pattern transfer etching process is an anisotropic etch. In one embodiment, a dry etching process such as, for example, reactive ion etching can be used. In another embodiment, a chemical etchant can be used. In still a further embodiment, a combination of dry etching and wet etching can be used. In some embodiments, the patterned resist material may be removed at this point of the present application by utilizing a resist removal process such as, for example, ashing. In yet other embodiments, the patterned resist may remain atop the hard mask portion 12 during the subsequent formation of the trench opening 11. In embodiments when a bulk semiconductor substrate is employed, the trench opening 11 exposes a sub-surface portion of the bulk semiconductor substrate. By "sub-surface" it is meant a surface of a material layer that is located between a topmost surface of the material layer and the bottommost surface of the material layer. In embodiments when an SOI substrate is employed, the trench opening 11 may stop on a topmost surface of the insulator layer.

The trench opening 11 is then formed into an upper semiconductor material portion of the semiconductor substrate 10 utilizing at least the hard mask portion 12 as an etch mask. The trench opening 11 can be formed utilizing one of the etching processes mentioned above in patterning the hard mask layer.

Figure 2A:
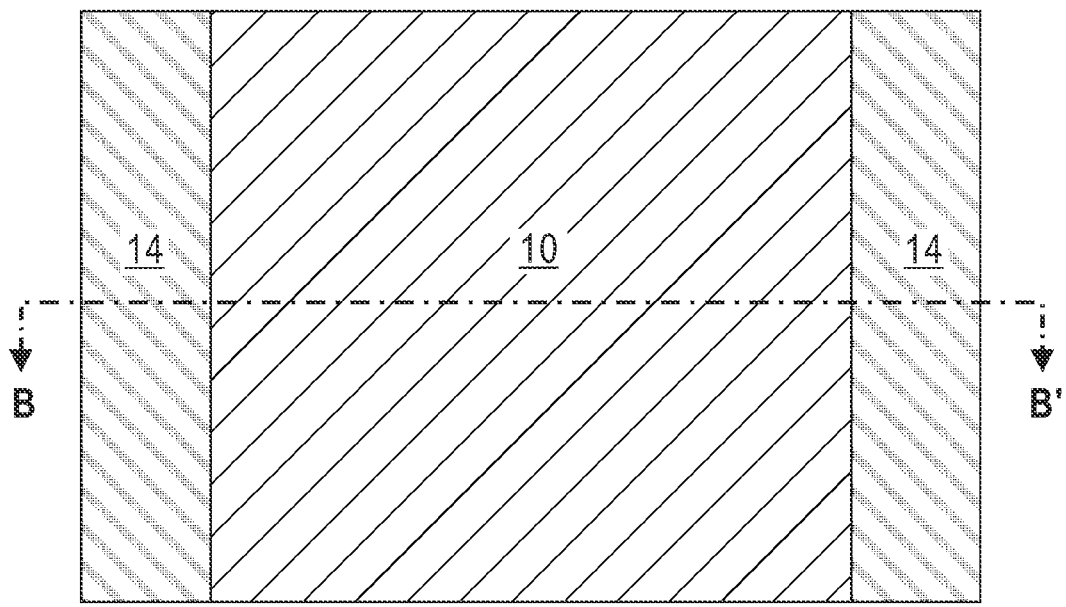
FIG. 2A is a top down view of the exemplary semiconductor structure of FIGS. 1A-1B after forming a trench isolation structure within the trench opening and surrounding the mesa region of the semiconductor substrate.
Figure 2B:
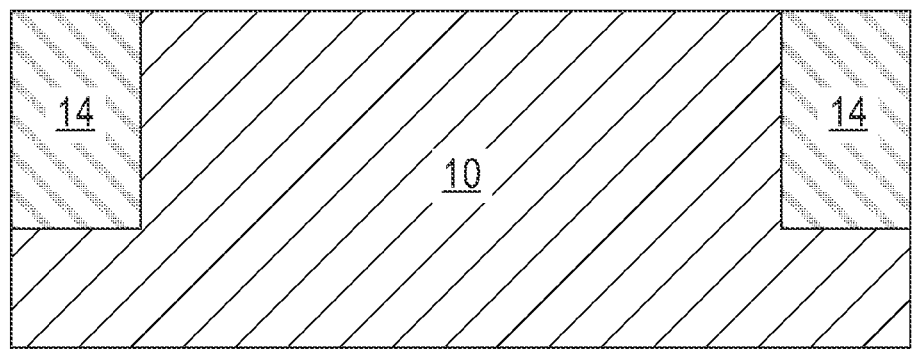
FIG. 2B is a cross sectional view of the exemplary semiconductor structure of FIG. 2A through vertical plane B-B'.

Referring now to FIGS. 2A-2B, there are illustrated the exemplary semiconductor structure of FIGS. 1A-1B after forming a trench isolation structure 14 within the trench opening 11 and surrounding the mesa region 10M of the semiconductor substrate 10. The trench isolation structure 14 may by formed by first filling the trench opening 11 with a trench dielectric material such as, for example, silicon dioxide. The trench opening 11 can be filled by utilizing a deposition process such, as for example, chemical vapor deposition (CVD) or plasma enhanced chemical vapor deposition (PECVD). A planarization process such as, for example, chemical mechanical polishing can then be used to remove any excess trench dielectric material that is formed above the topmost surface of the mesa region 10M of the semiconductor substrate 10 and also to remove the hard mask portion 12 from above the mesa region 10M of the semiconductor substrate 10.

Figure 3A:
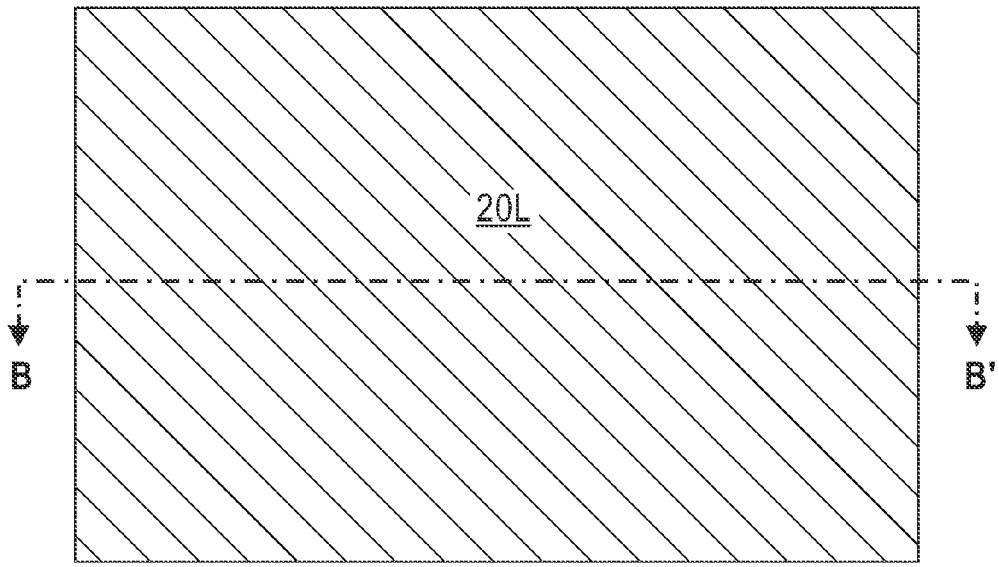
FIG. 3A is a top down view of the exemplary semiconductor structure of FIGS. 2A-2B after formation of a gate dielectric layer and a sacrificial gate stack including, from bottom to top, a sacrificial gate layer, and a sacrificial gate cap layer.
Figure 3B:
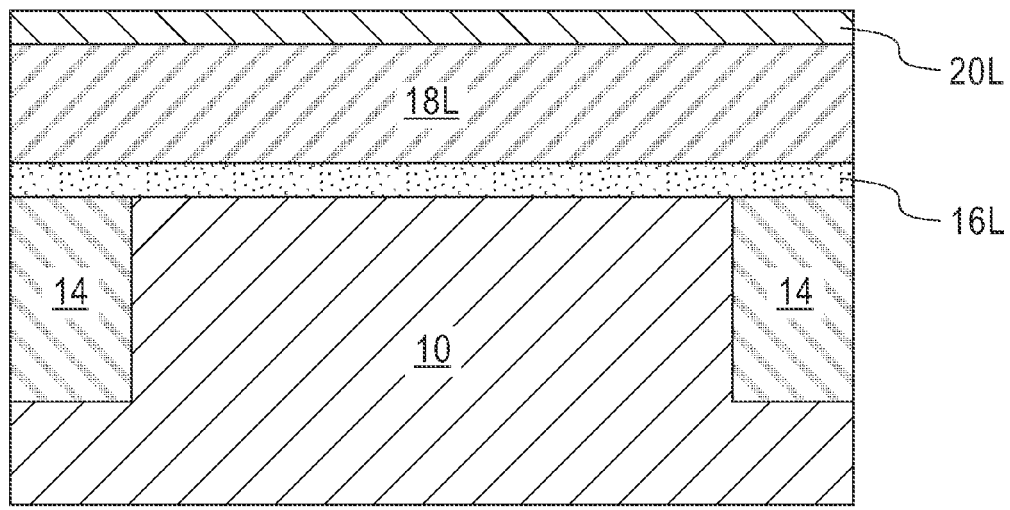
FIG. 3B is a cross sectional view of the exemplary semiconductor structure of FIG. 3A through vertical plane B-B'.

Referring now to FIGS. 3A-3B, there are illustrated various views of the exemplary semiconductor structure of FIGS. 2A-2B after formation of a gate dielectric layer 16L and a sacrificial gate stack (18L, 20L) including, from bottom to top, a sacrificial gate layer 18L, and a sacrificial gate cap layer 20L.

As is shown, the gate dielectric layer 16L is continuous layer that covers the entirety of the mesa region 10M of the semiconductor substrate 10 as well as the trench isolation structure 14. The gate dielectric layer 16L includes any gate dielectric material. The gate dielectric material that provides the gate dielectric layer 16L can be an oxide, nitride, and/or oxynitride. In one example, the gate dielectric material that provides the gate dielectric layer 16L can be a high-k material having a dielectric constant greater than silicon dioxide. Exemplary high-k dielectrics include, but are not limited to, $HfO_2$, $ZrO_2$, $La_2O_3$, $Al_2O_3$, $TiO_2$, $SrTiO_3$, $LaAlO_3$, $Y_2O_3$, $HfO_xN_y$, $ZrO_xN_y$, $La_2O_xN_y$, $Al_2O_xN_y$, $TiO_xN_y$, $SrTiO_xN_y$, $LaAlO_xN_y$, $Y_2O_xN_y$, $SiON$, $SiN_x$, a silicate thereof, and an alloy thereof. Each value of x is independently from 0.5 to 3 and each value of y is independently from 0 to 2. In some embodiments, a multilayered gate dielectric structure comprising different gate dielectric materials, e.g., silicon dioxide, and a high-k gate dielectric, can be formed and used as the gate dielectric layer 16L.

The gate dielectric material used in providing the gate dielectric layer 16L can be formed by any deposition process including, for example, chemical vapor deposition (CVD), plasma enhanced chemical vapor deposition (PECVD), physical vapor deposition (PVD), sputtering, or atomic layer deposition. In one embodiment of the present application, the gate dielectric material used in providing the gate dielectric layer 16L can have a thickness in a range from 1 nm to 10 nm. Other thicknesses that are lesser than, or greater than, the aforementioned thickness range can also be employed for the gate dielectric material.

Next, the sacrificial gate structure (18L, 20L) is formed on the gate dielectric layer 16L. Although the present application describes and illustrates the presence of a sacrificial gate cap layer 20L such a layer can be omitted in some embodiments of the present application. The sacrificial gate layer 18L of the sacrificial gate structure may include any material having an etch selectivity that is different from the underlying gate dielectric layer 16L. In one embodiment of the present application, the sacrificial gate layer 18L may be composed of doped or undoped polysilicon. In another embodiment of the present application, the sacrificial gate layer 18L may be composed of doped or undoped amorphous silicon. In yet other embodiments of the present application, the sacrificial gate layer 18L may be a conductive material such as, for example, an elemental metal (e.g., tungsten, titanium, tantalum, aluminum, nickel, ruthenium, palladium and platinum), an alloy of at least two elemental metals, an elemental metal nitride (e.g., tungsten nitride, aluminum nitride, and titanium nitride), an elemental metal silicide (e.g., tungsten silicide, nickel silicide, and titanium silicide) or multilayered combinations thereof.

The sacrificial gate layer 18L can be formed utilizing a deposition process including, for example, chemical vapor deposition (CVD), plasma enhanced chemical vapor deposition (PECVD), physical vapor deposition (PVD), sputtering, atomic layer deposition (ALD) or other like deposition processes. When a metal silicide is formed, a conventional silicidation process is employed. In one embodiment, the sacrificial gate layer 18L has a thickness from 1 nm to 100 nm. Other thicknesses that are lesser than, or greater than, the aforementioned thickness range can also be employed for sacrificial gate layer 18L.

If present, the sacrificial gate cap layer 20L can be composed of one of the hard mask materials mentioned above. For example, the sacrificial gate cap layer 20L may include silicon dioxide, silicon nitride, and/or silicon oxynitride. The hard mask material that provides the sacrificial gate cap layer 20L can be formed utilizing a conventional deposition process such as, for example, chemical vapor deposition or plasma enhanced chemical vapor deposition. When present, the sacrificial gate cap layer 20L can have a thickness from 5 nm to 20 nm. Other thicknesses that are lesser than, or greater than, the aforementioned thickness range can also be employed as the thickness of the sacrificial gate cap layer 20L.

Figure 4A:
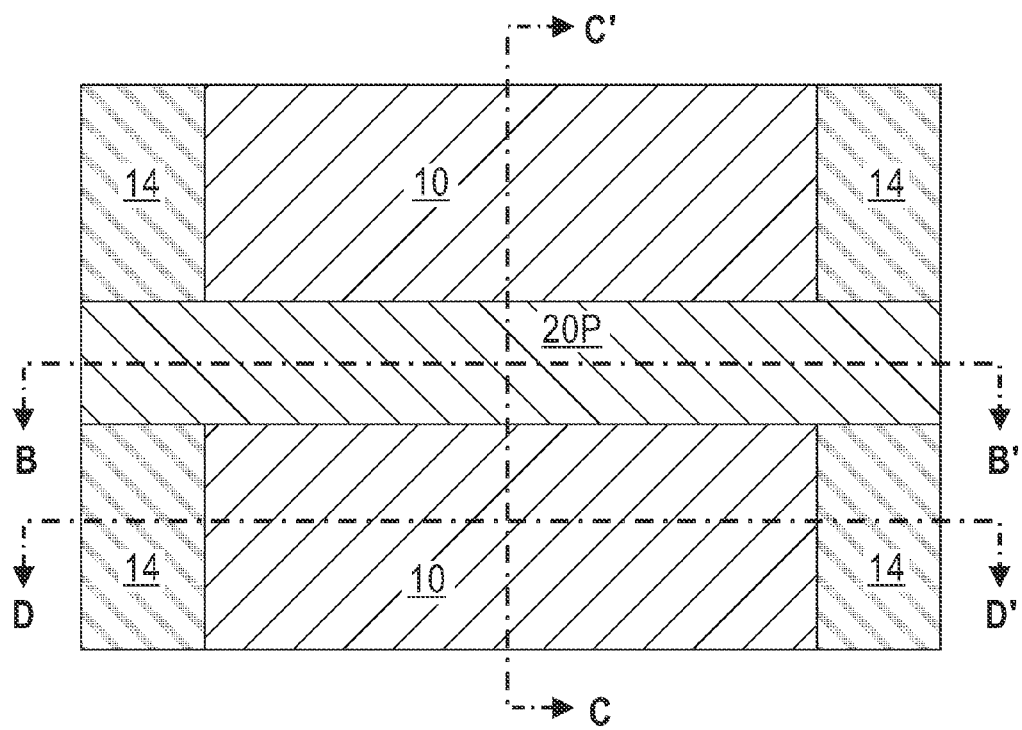
FIG. 4A is a top down view of the exemplary semiconductor structure of FIGS. 3A-3B after patterning the sacrificial gate stack and the underlying gate dielectric layer to provide a sacrificial gate structure located on a gate dielectric portion.
Figure 4B:
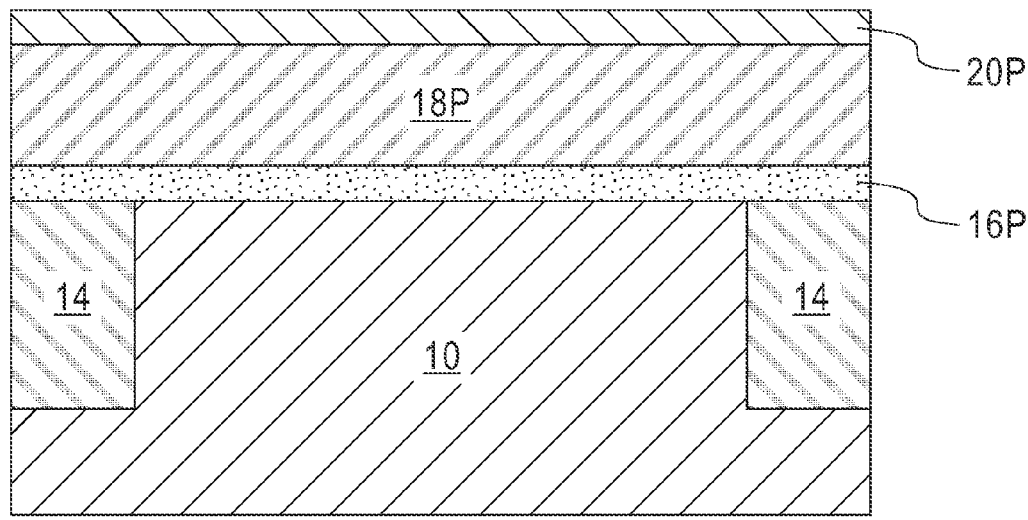
FIG. 4B is a cross sectional view of the exemplary semiconductor structure of FIG. 4A through vertical plane B-B'.
Figure 4C:
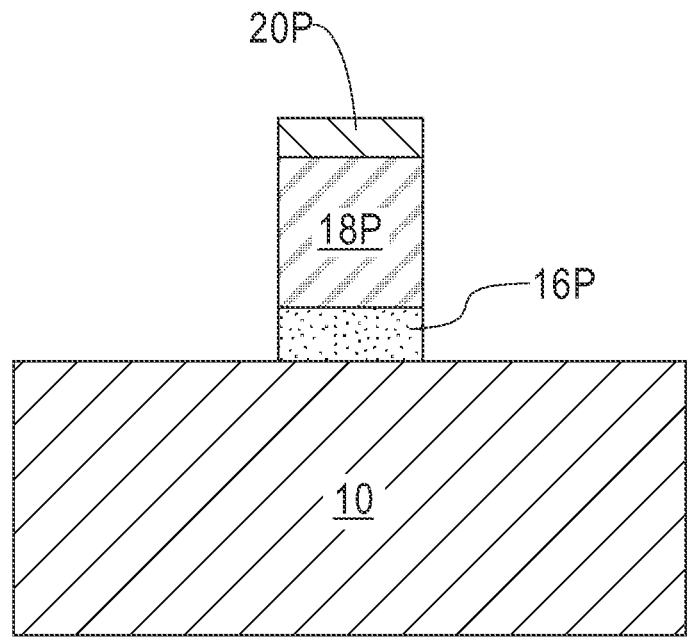
FIG. 4C is a cross sectional view of the exemplary semiconductor structure of FIG. 4A through vertical plane C-C'.
Figure 4D:
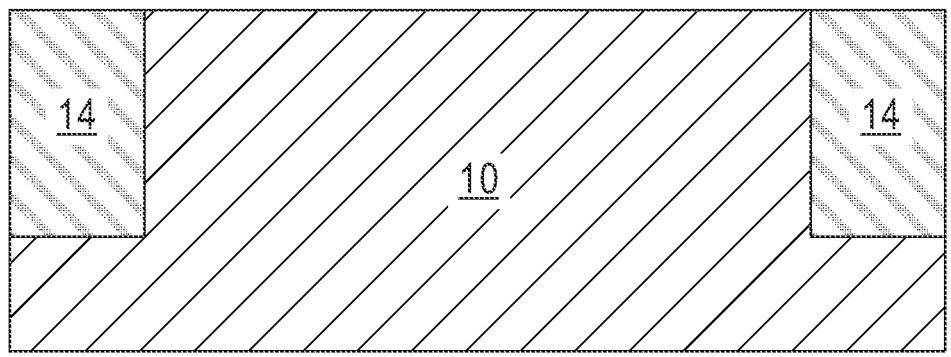
FIG. 4D is a cross sectional view of the exemplary semiconductor structure of FIG. 4A through vertical plane D-D'.
Figure 5A:
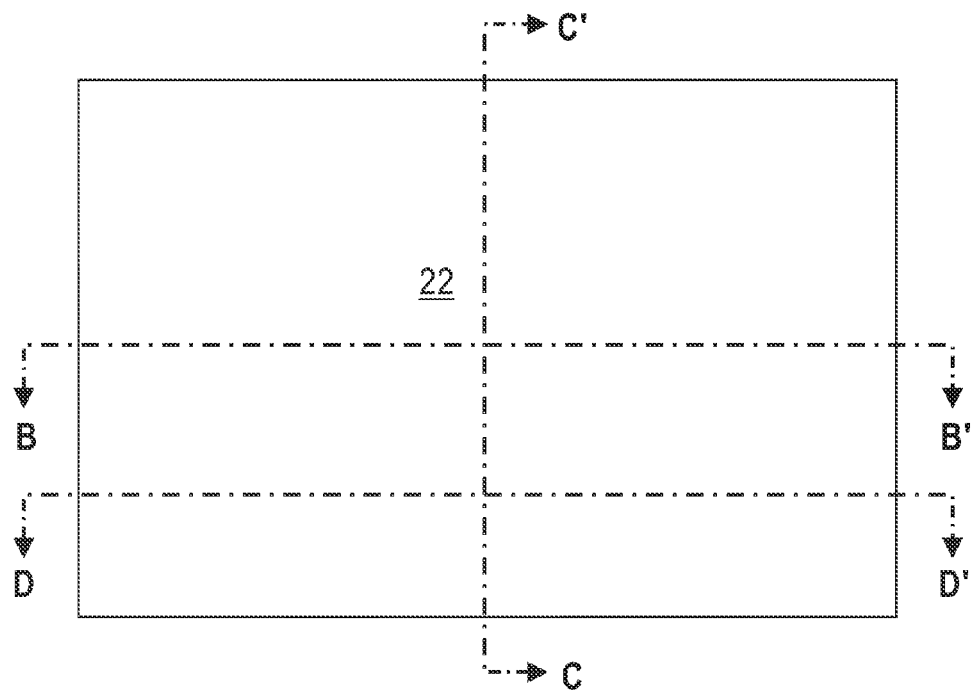
FIG. 5A is a top down view of the exemplary semiconductor structure of FIGS. 4A-4D after forming a spacer dielectric material layer.
Figure 5B:
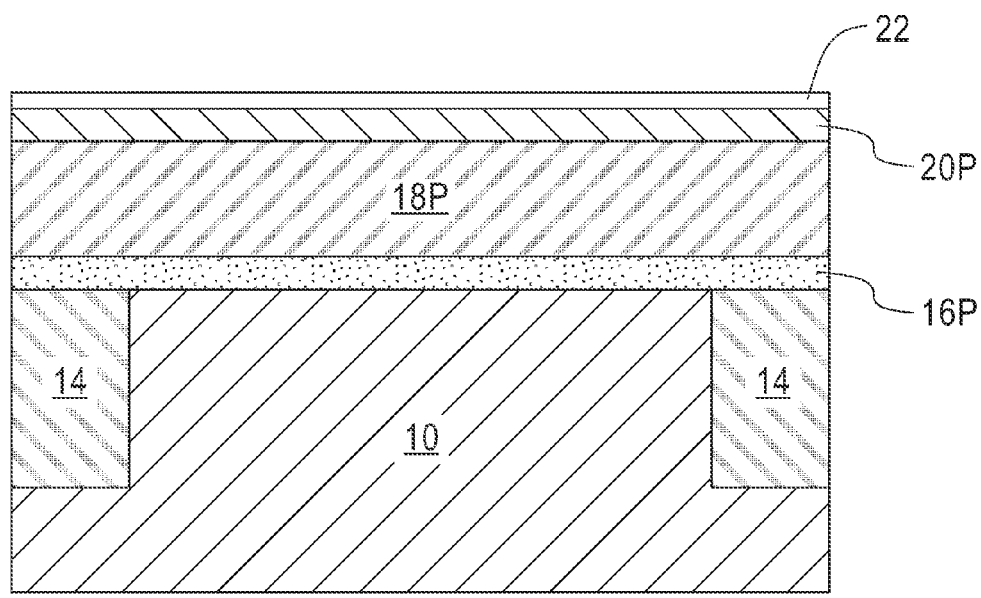
FIG. 5B is a cross sectional view of the exemplary semiconductor structure of FIG. 5A through vertical plane B-B'.
Figure 5C:
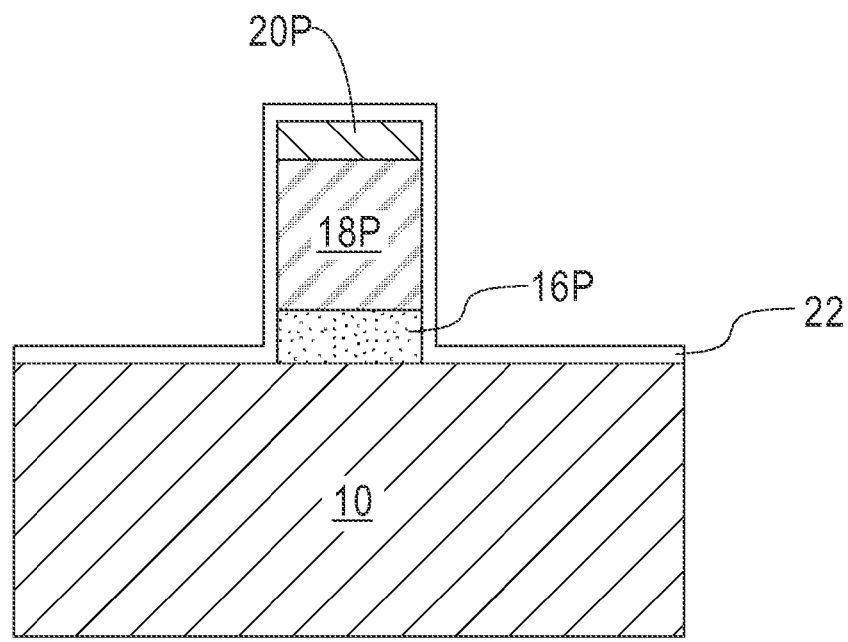
FIG. 5C is a cross sectional view of the exemplary semiconductor structure of FIG. 5A through vertical plane C-C'.
Figure 5D:
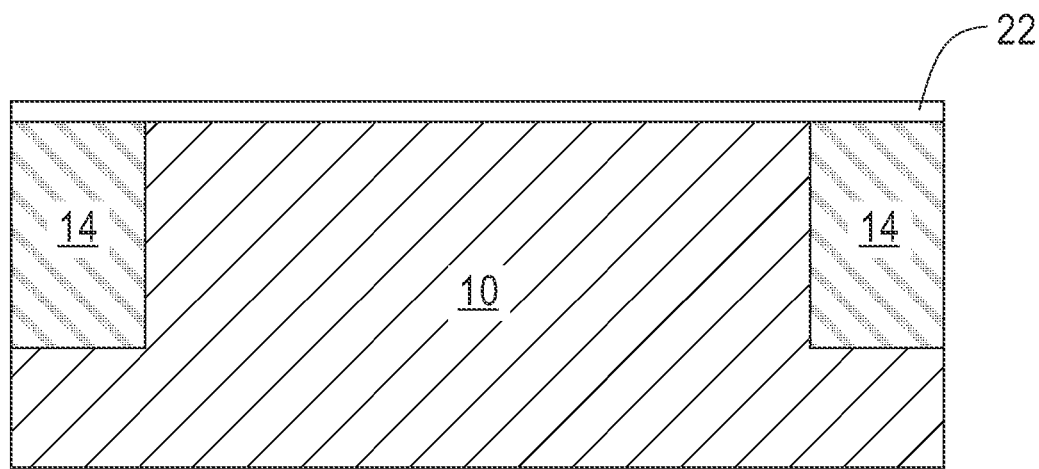
FIG. 5D is a cross sectional view of the exemplary semiconductor structure of FIG. 5A through vertical plane D-D'.
Figure 6A:
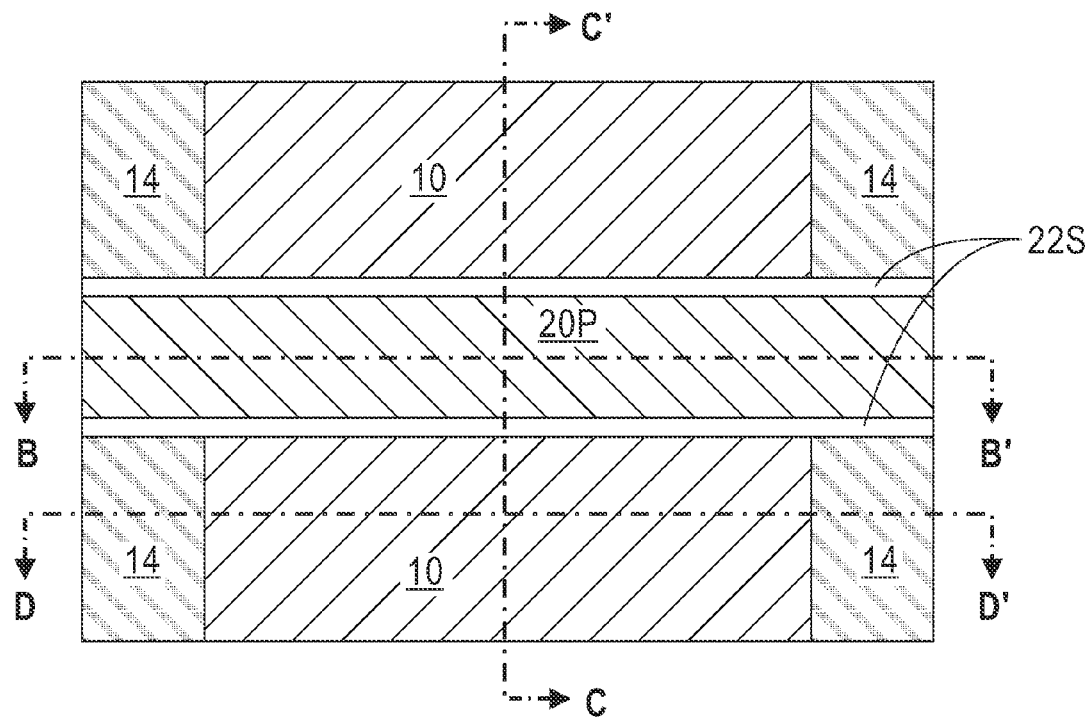
FIG. 6A is a top down view of the exemplary semiconductor structure of FIGS. 5A-5D after patterning the spacer dielectric material layer into a dielectric spacer which is located on sidewall surfaces of the sacrificial gate structure and the gate dielectric portion.
Figure 6B:
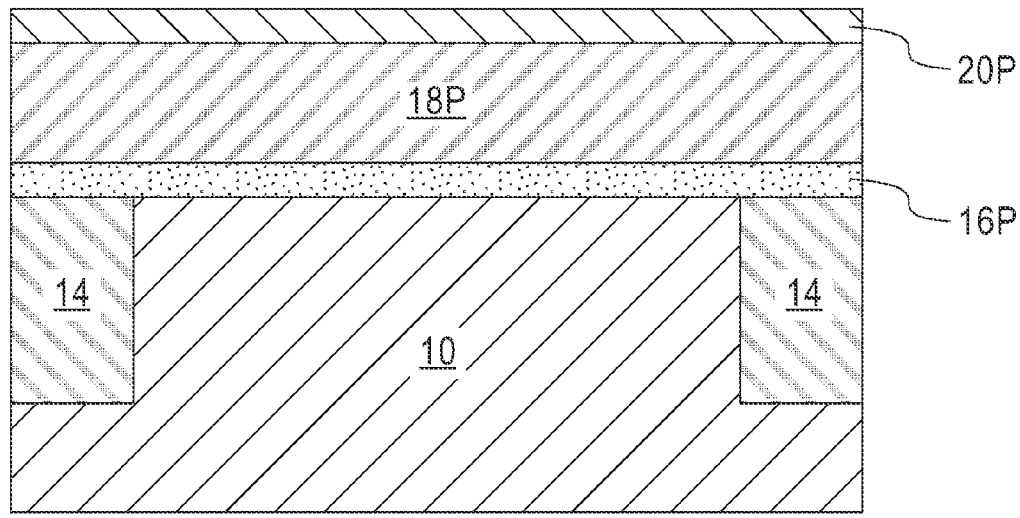
FIG. 6B is a cross sectional view of the exemplary semiconductor structure of FIG. 6A through vertical plane B-B'.
Figure 6C:
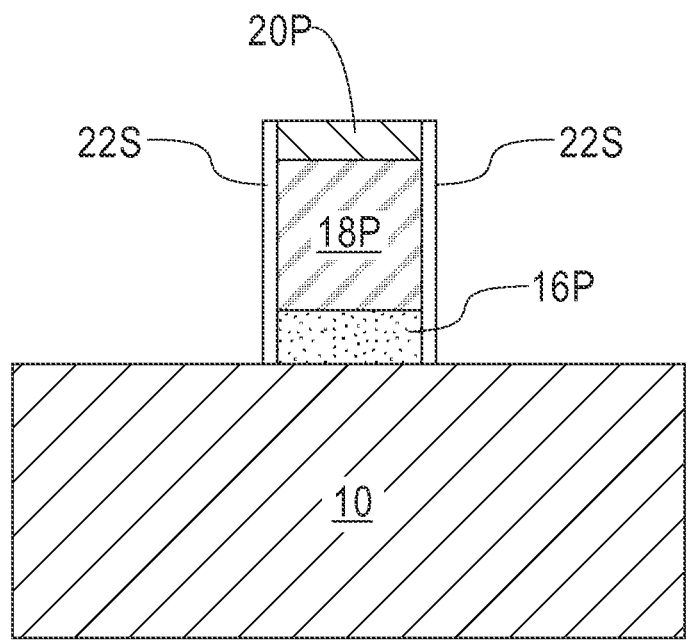
FIG. 6C is a cross sectional view of the exemplary semiconductor structure of FIG. 6A through vertical plane C-C'.
Figure 6D:
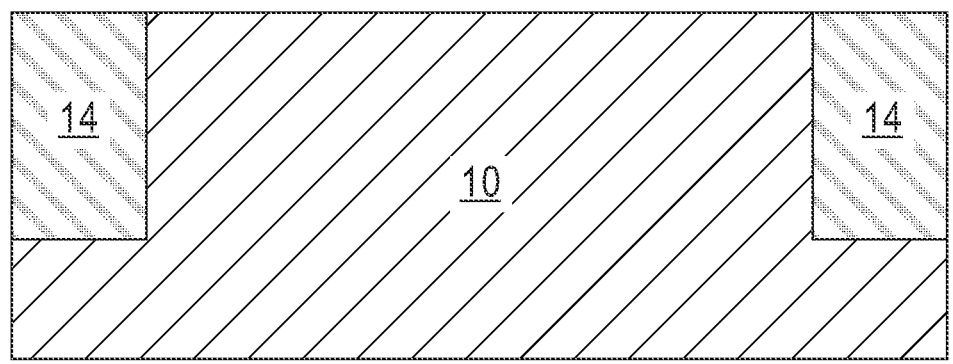
FIG. 6D is a cross sectional view of the exemplary semiconductor structure of FIG. 6A through vertical plane D-D'.
Figure 7A:
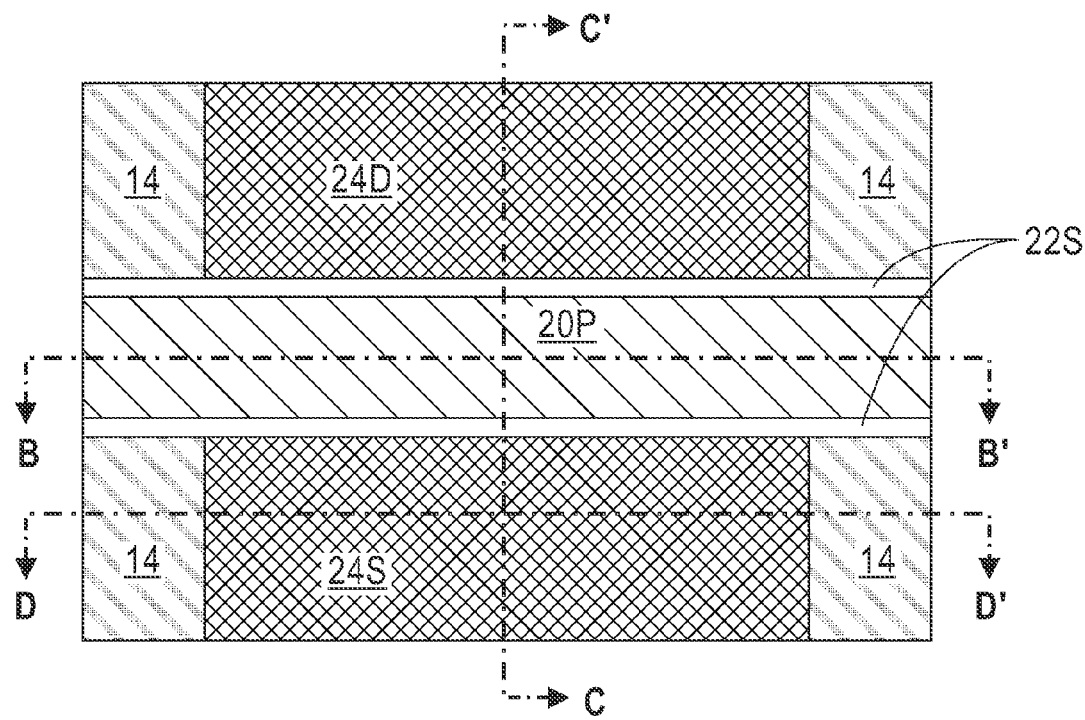
FIG. 7A is a top down view of the exemplary semiconductor structure of FIGS. 6A-6D after forming a doped epitaxial source semiconductor material on a first side of the sacrificial gate structure and a doped epitaxial drain semiconductor material on a second side of the sacrificial gate structure, the second side is opposite the first side.
Figure 7B:
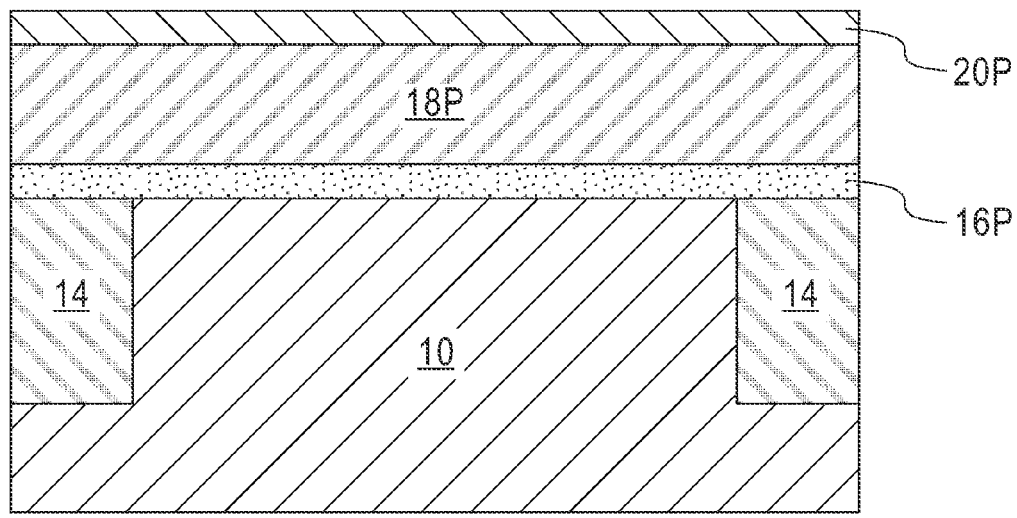
FIG. 7B is a cross sectional view of the exemplary semiconductor structure of FIG. 7A through vertical plane B-B'.
Figure 7C:
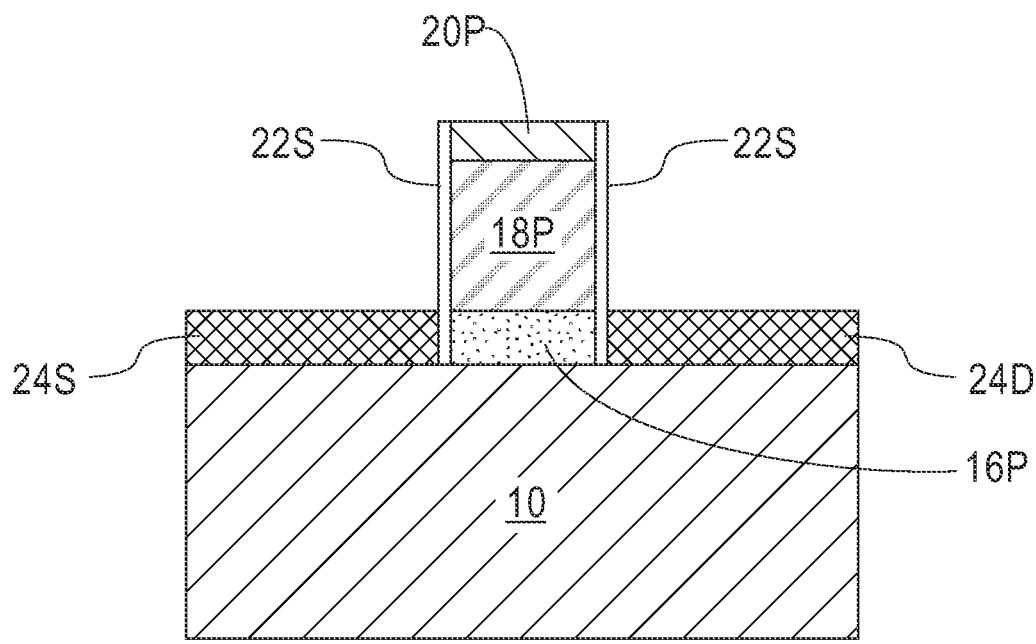
FIG. 7C is a cross sectional view of the exemplary semiconductor structure of FIG. 7A through vertical plane C-C'.
Figure 7D:
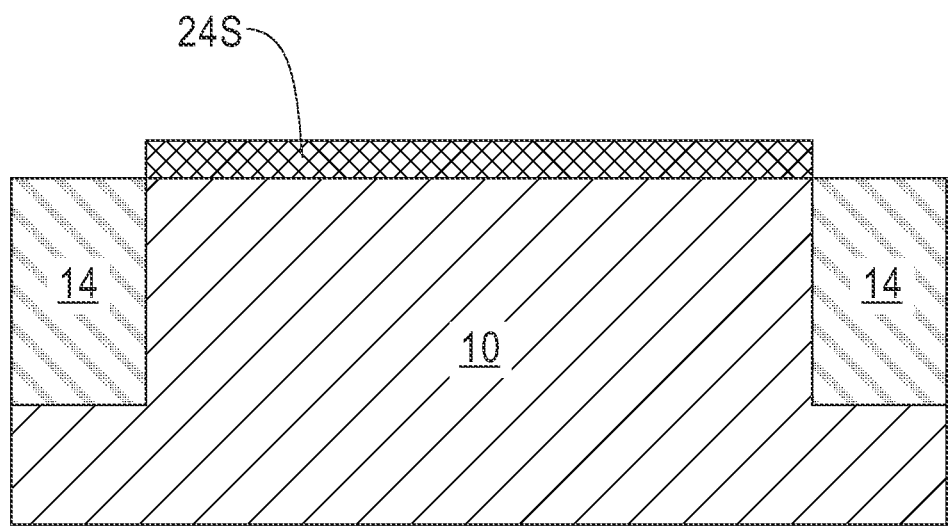
FIG. 7D is a cross sectional view of the exemplary semiconductor structure of FIG. 7A through vertical plane D-D'.
Figure 8A:
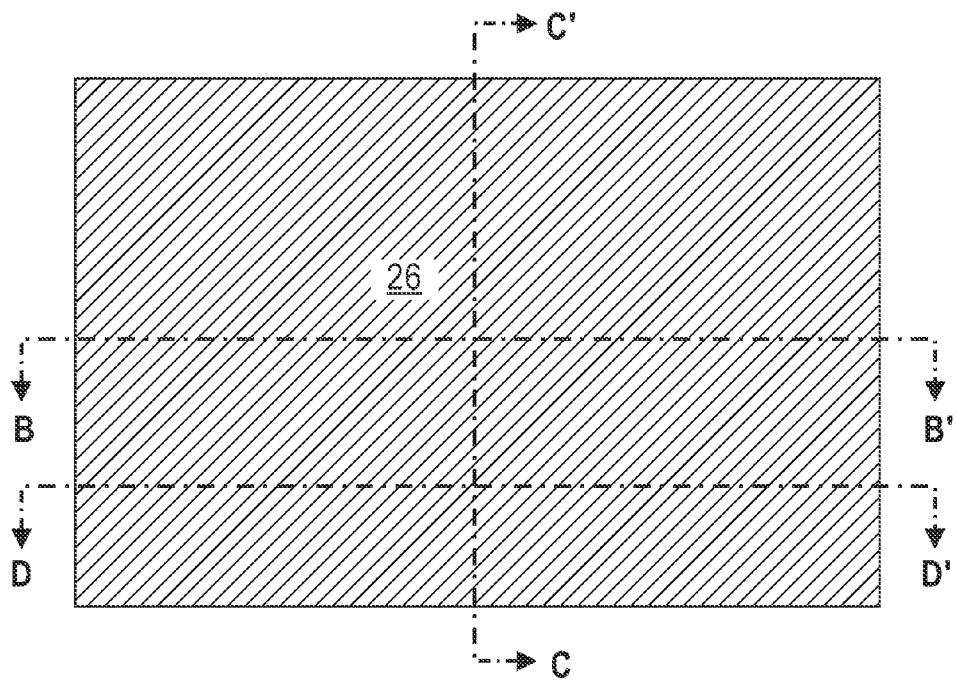
FIG. 8A is a top down view of the exemplary semiconductor structure of FIGS. 7A-7D after forming a hard mask layer.
Figure 8B:
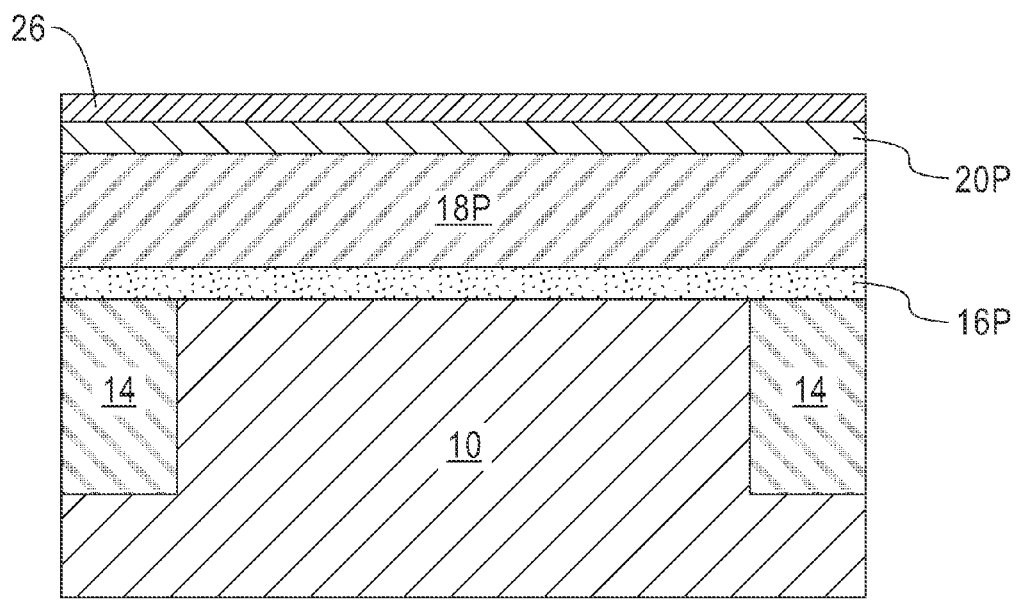
FIG. 8B is a cross sectional view of the exemplary semiconductor structure of FIG. 8A through vertical plane B-B'.
Figure 8C:
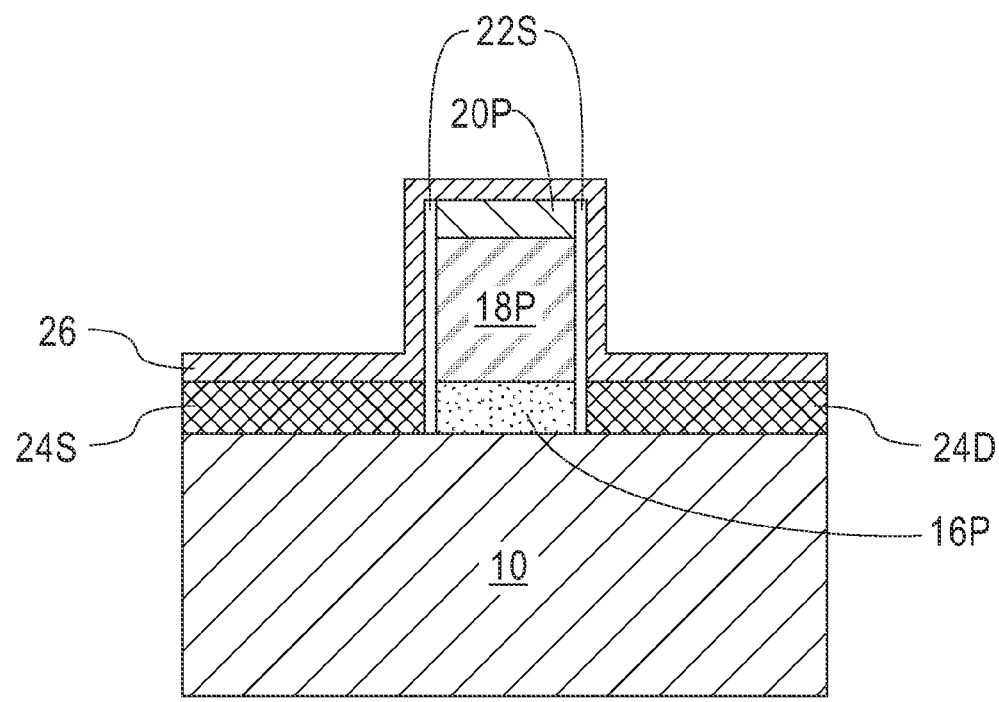
FIG. 8C is a cross sectional view of the exemplary semiconductor structure of FIG. 8A through vertical plane C-C'.
Figure 8D:
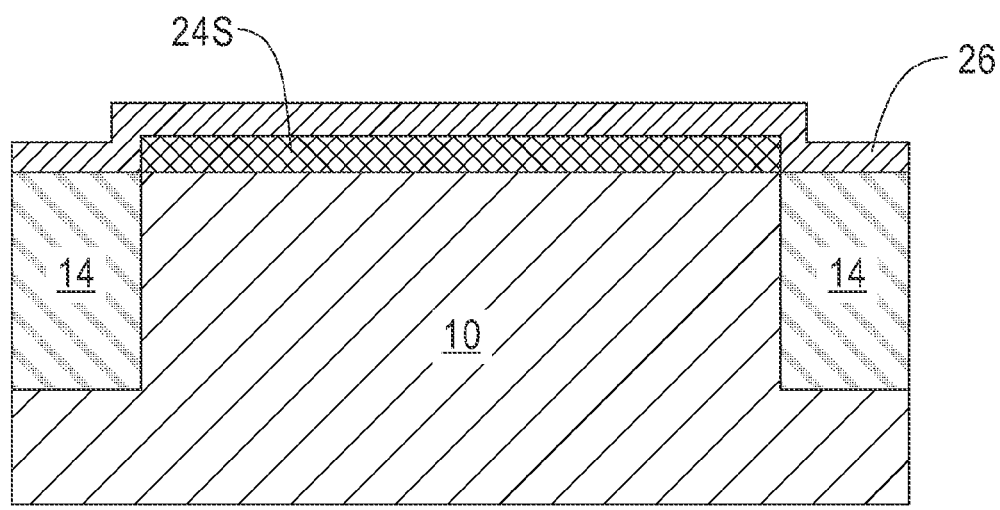
FIG. 8D is a cross sectional view of the exemplary semiconductor structure of FIG. 8A through vertical plane D-D'.
Figure 9A:
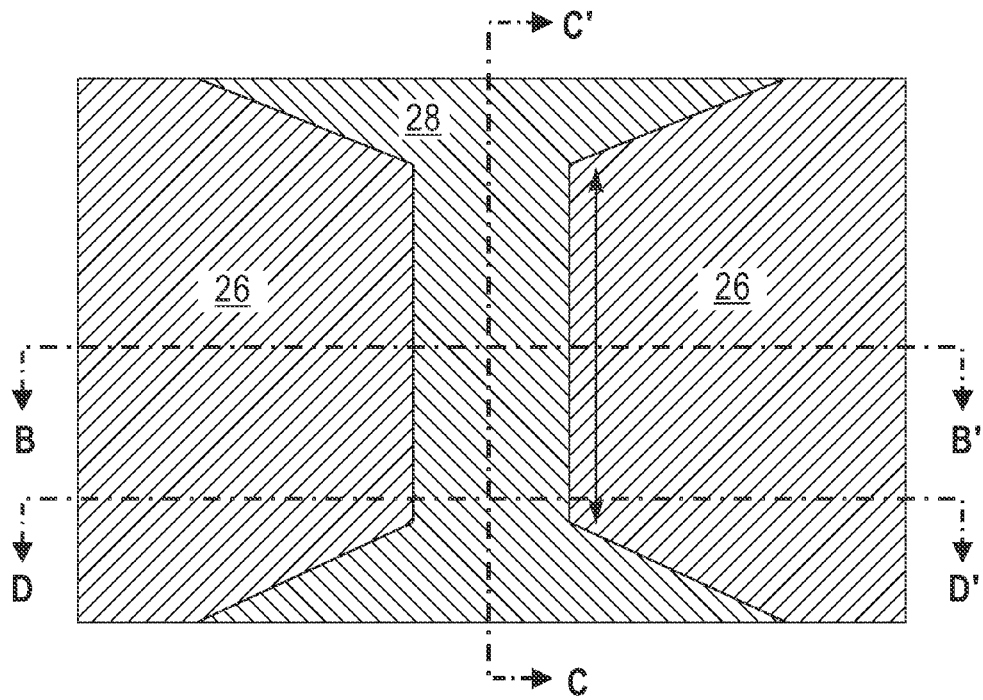
FIG. 9A is a top down view of the exemplary semiconductor structure of FIGS. 8A-8D after forming a sacrificial gate cut mask on a surface of the hard mask layer.
Figure 9B:
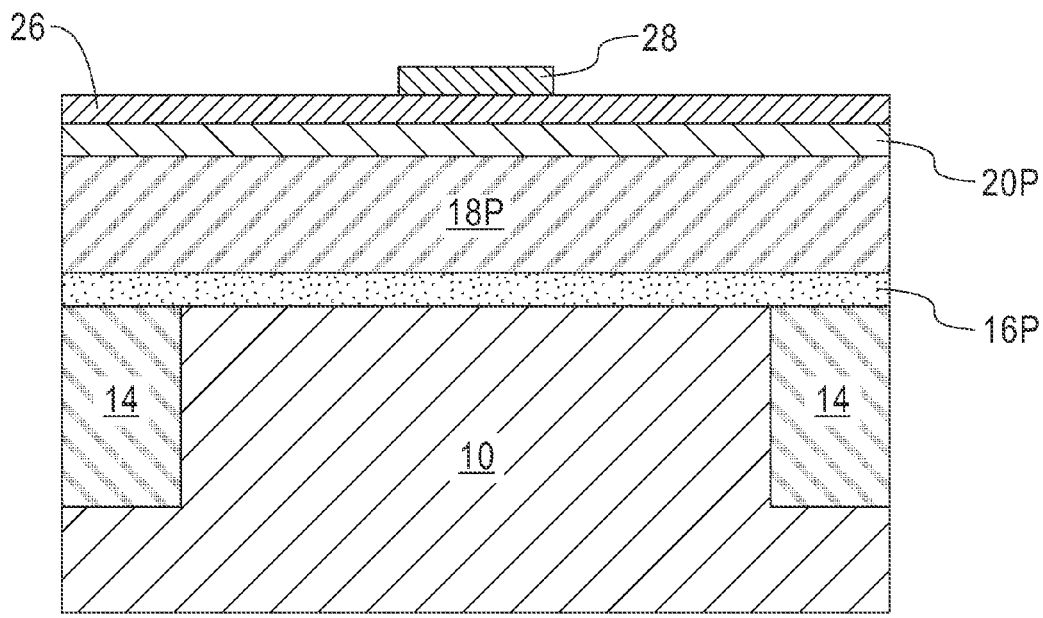
FIG. 9B is a cross sectional view of the exemplary semiconductor structure of FIG. 9A through vertical plane B-B'.
Figure 9C:
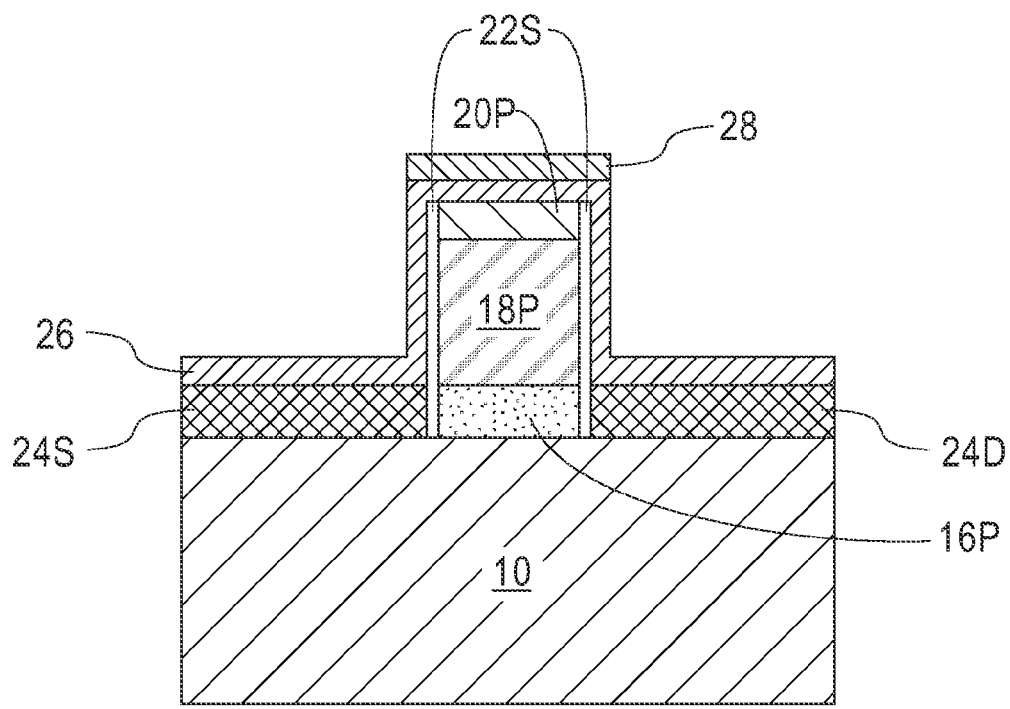
FIG. 9C is a cross sectional view of the exemplary semiconductor structure of FIG. 9A through vertical plane C-C'.
Figure 9D:
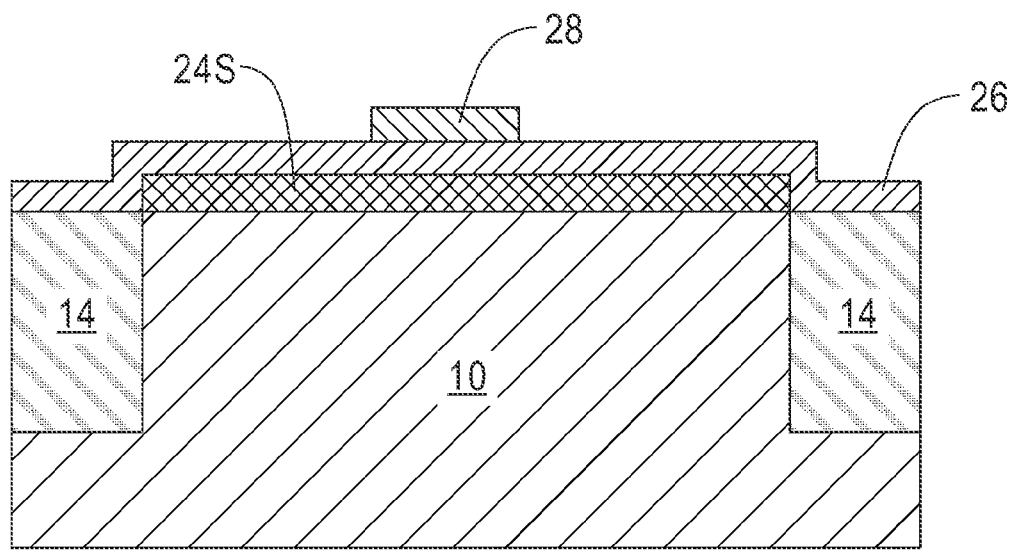
FIG. 9D is a cross sectional view of the exemplary semiconductor structure of FIG. 9A through vertical plane D-D'.
Figure 10A:
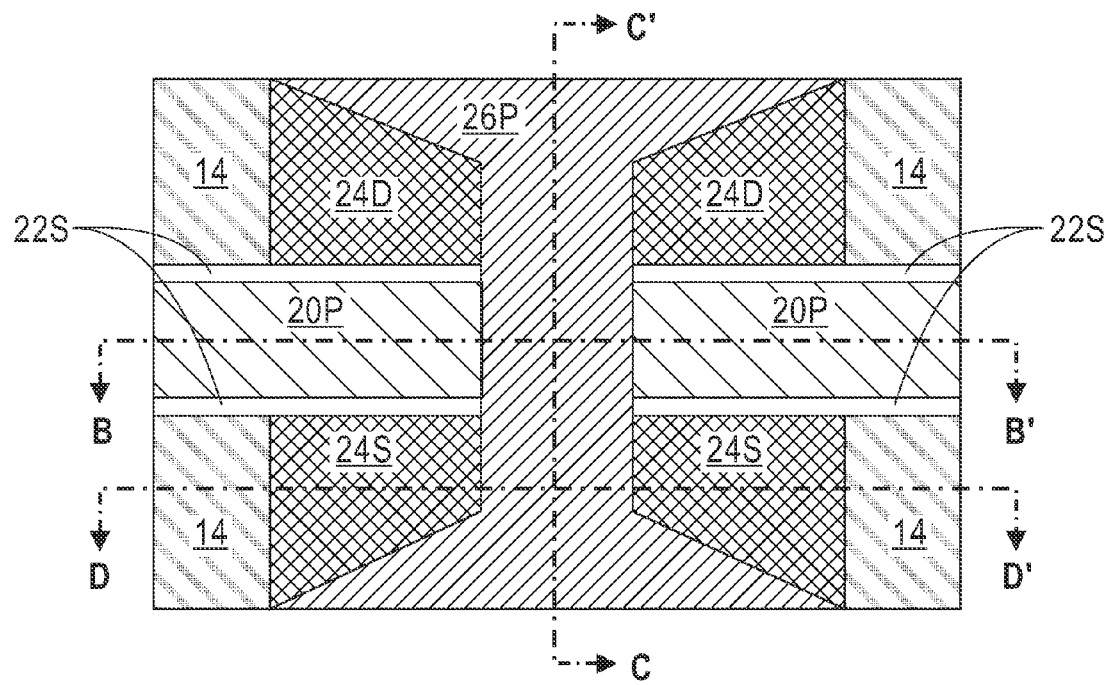
FIG. 10A is a top down view of the exemplary semiconductor structure of FIGS. 9A-9D after patterning the hard mask layer utilizing the sacrificial gate cut mask as an etch mask, and removing the sacrificial gate cut mask.
Figure 10B:
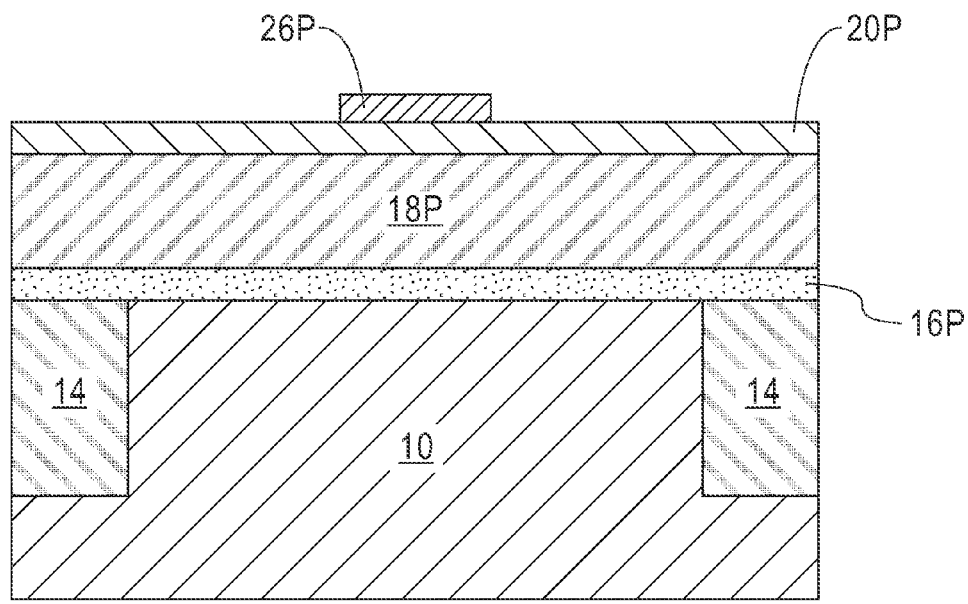
FIG. 10B is a cross sectional view of the exemplary semiconductor structure of FIG. 10A through vertical plane B-B'.
Figure 10C:
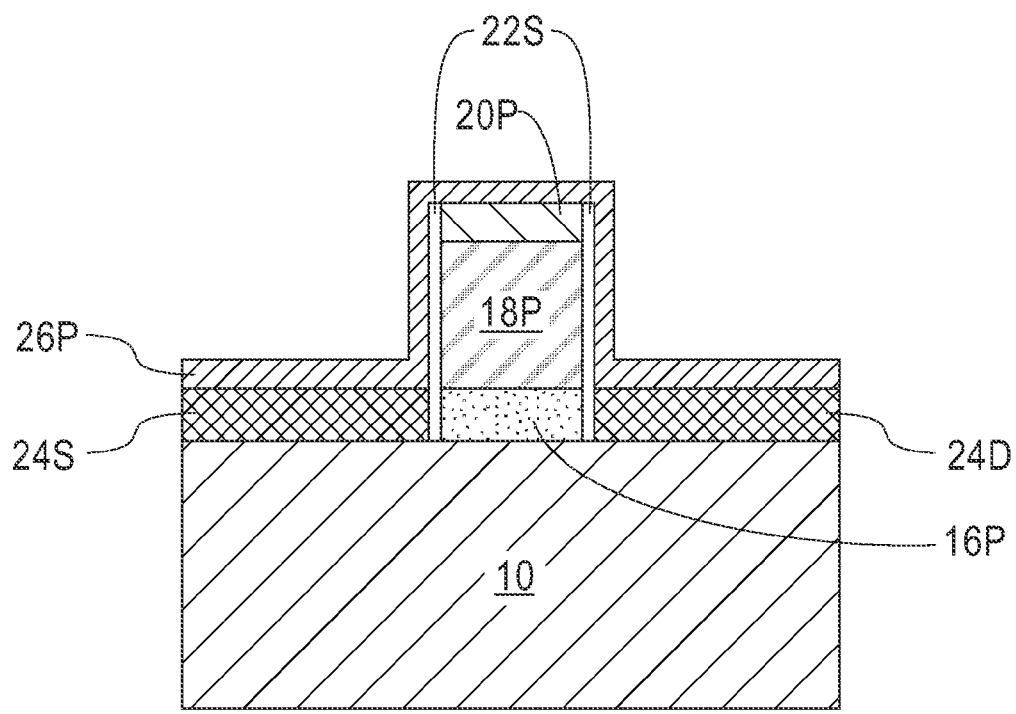
FIG. 10C is a cross sectional view of the exemplary semiconductor structure of FIG. 10A through vertical plane C-C'.
Figure 10D:
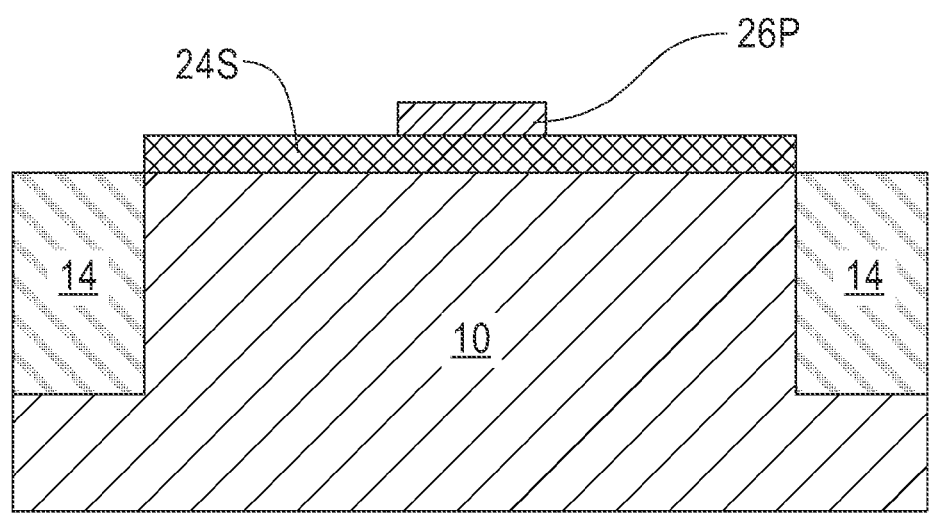
FIG. 10D is a cross sectional view of the exemplary semiconductor structure of FIG. 10A through vertical plane D-D'.
Figure 11A:
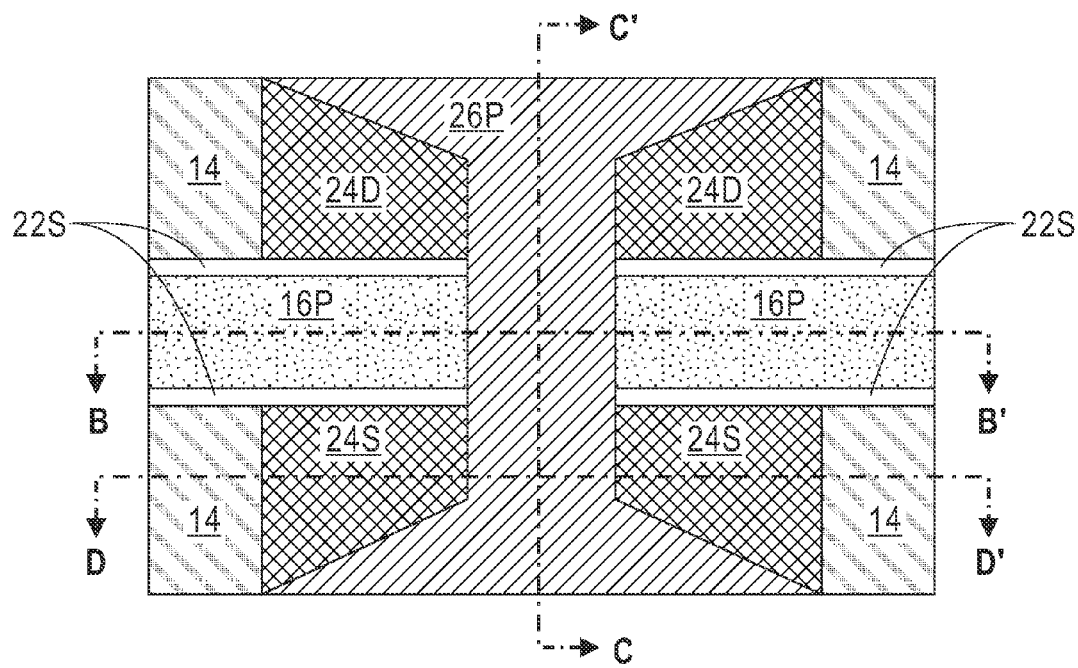
FIG. 11A is a top down view of the exemplary semiconductor structure of FIGS. 10A-10D after cutting the sacrificial gate structure utilizing the remaining hard mask layer as an etch mask.
Figure 11B:
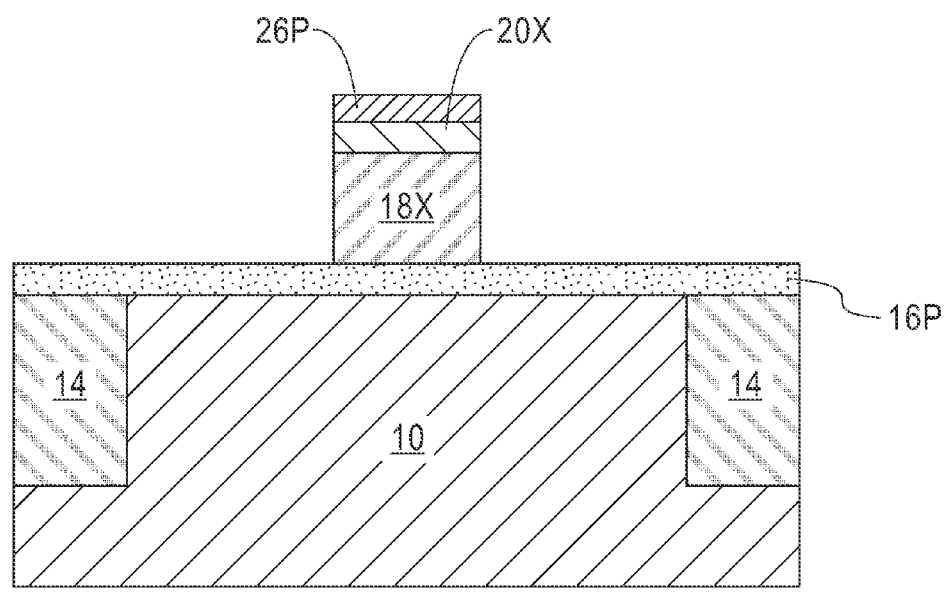
FIG. 11B is a cross sectional view of the exemplary semiconductor structure of FIG. 11A through vertical plane B-B'.
Figure 11C:
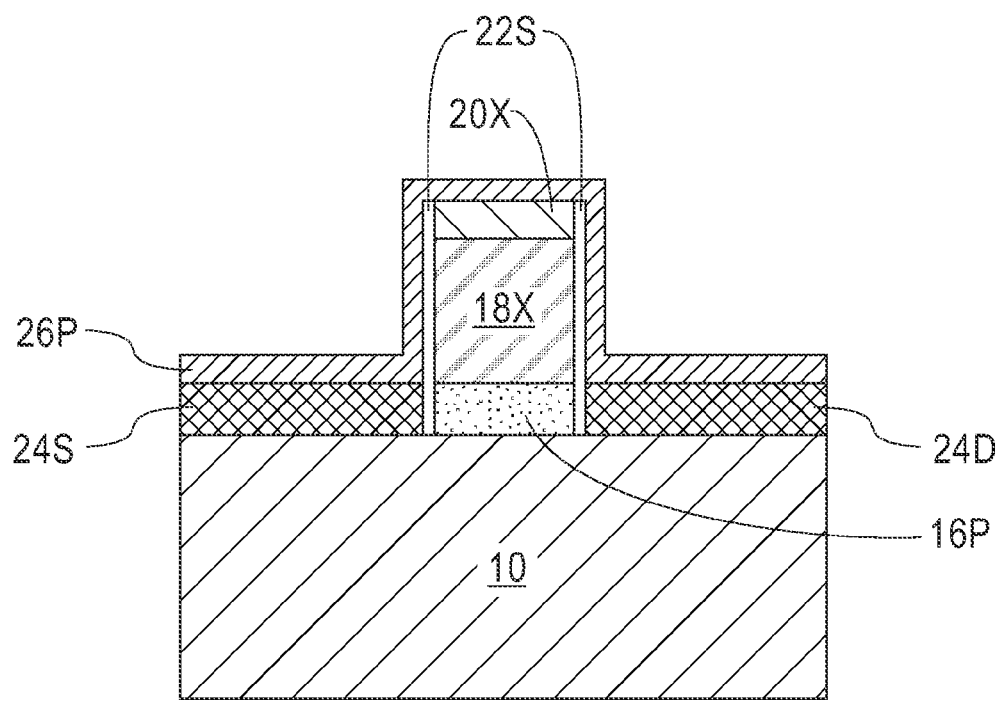
FIG. 11C is a cross sectional view of the exemplary semiconductor structure of FIG. 11A through vertical plane C-C'.
Figure 11D:
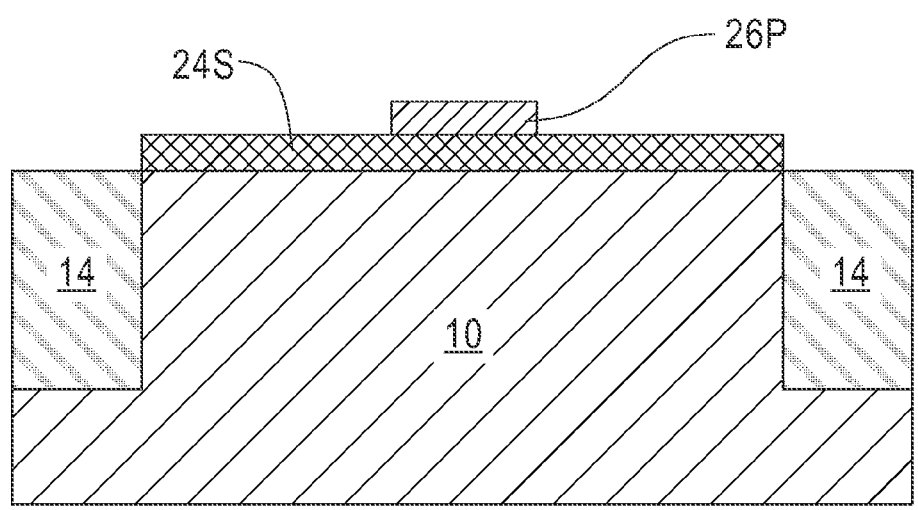
FIG. 11D is a cross sectional view of the exemplary semiconductor structure of FIG. 11A through vertical plane D-D'.
Figure 12A:
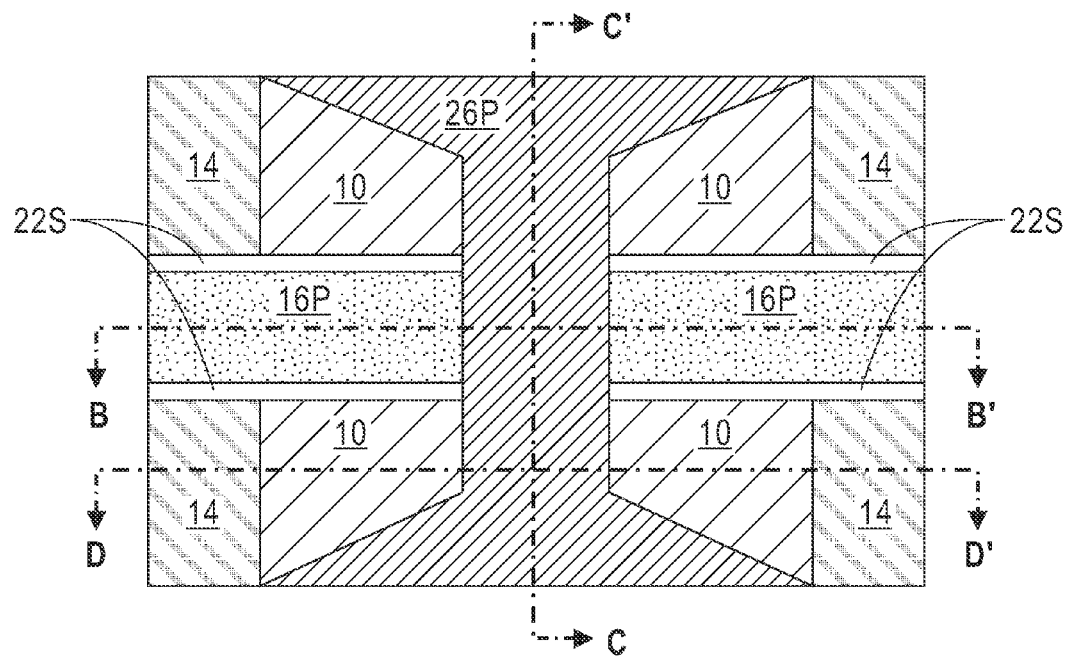
FIG. 12A is a top down view of the exemplary semiconductor structure of FIGS. 11A-11D after removing exposed portions of the doped epitaxial source and drain semiconductor materials.
Figure 12B:
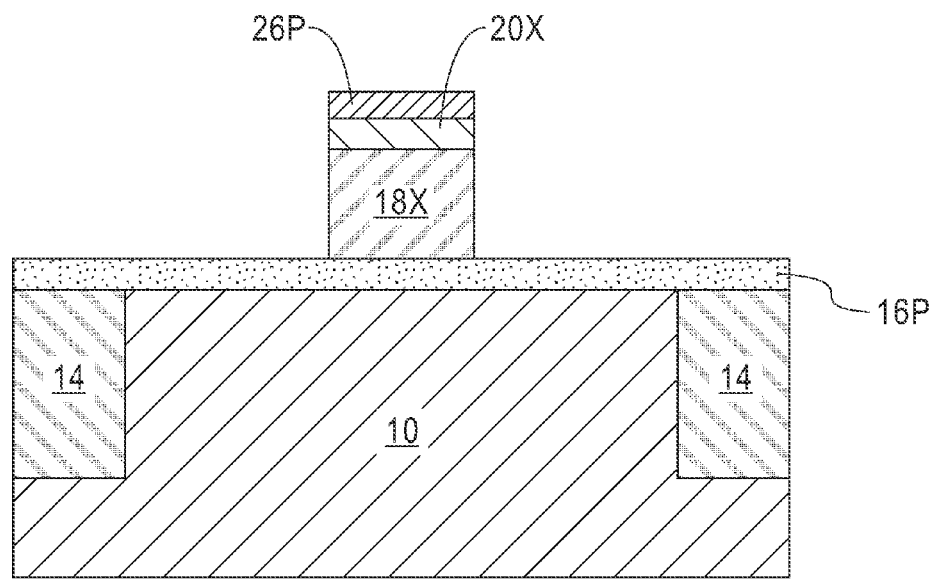
FIG. 12B is a cross sectional view of the exemplary semiconductor structure of FIG. 12A through vertical plane B-B'.
Figure 12C:
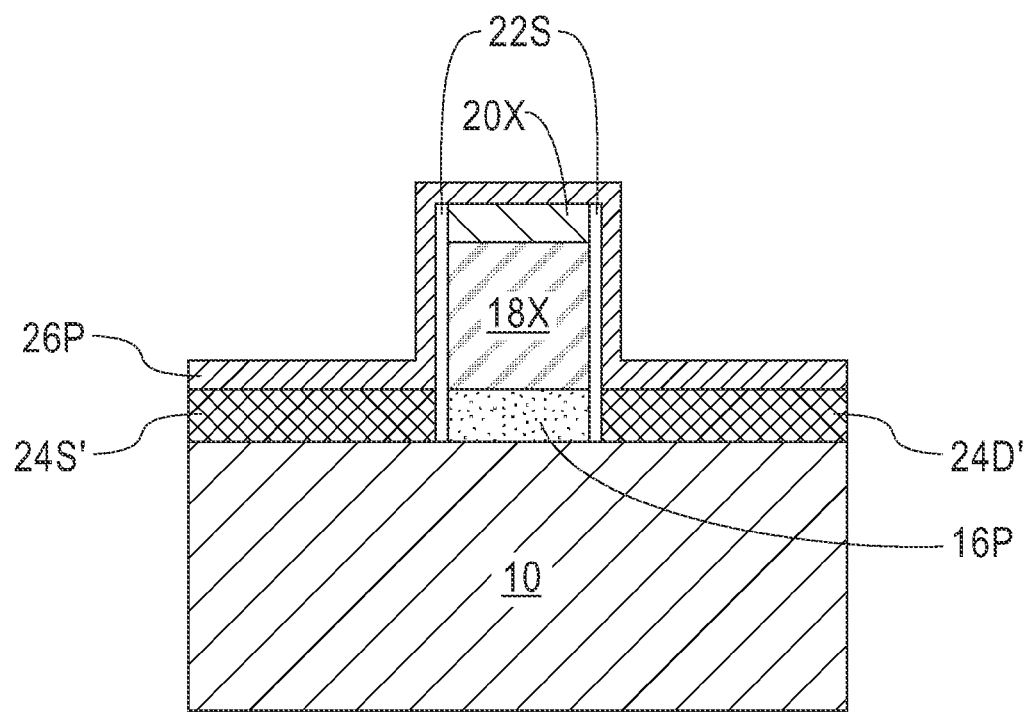
FIG. 12C is a cross sectional view of the exemplary semiconductor structure of FIG. 12A through vertical plane C-C'.
Figure 12D:
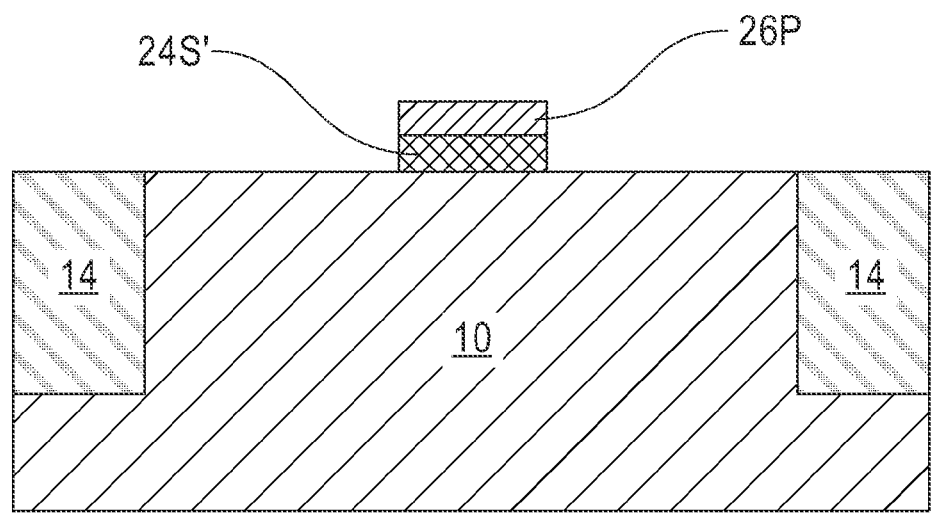
FIG. 12D is a cross sectional view of the exemplary semiconductor structure of FIG. 12A through vertical plane D-D'.
Figure 13A:
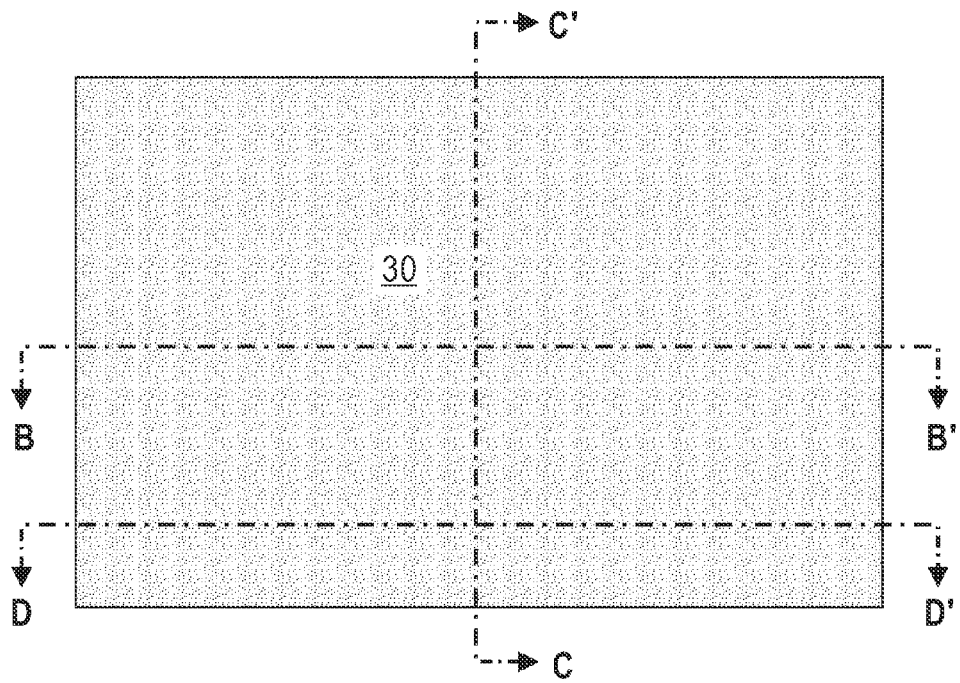
FIG. 13A is a top down view of the exemplary semiconductor structure of FIGS. 12A-12D after forming a dielectric material liner.
Figure 13B:
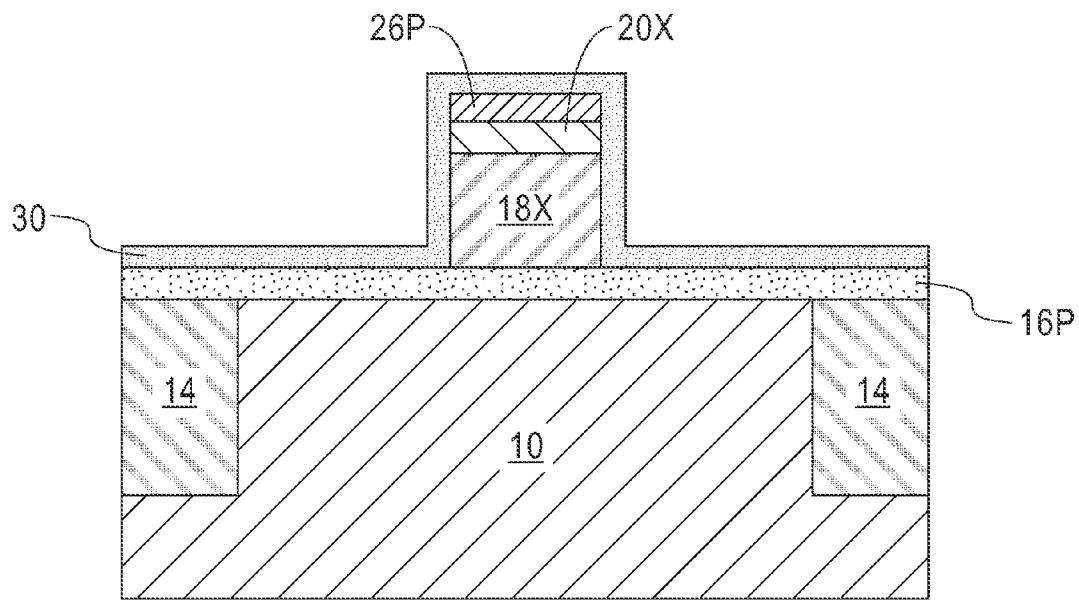
FIG. 13B is a cross sectional view of the exemplary semiconductor structure of FIG. 13A through vertical plane B-B'.
Figure 13C:
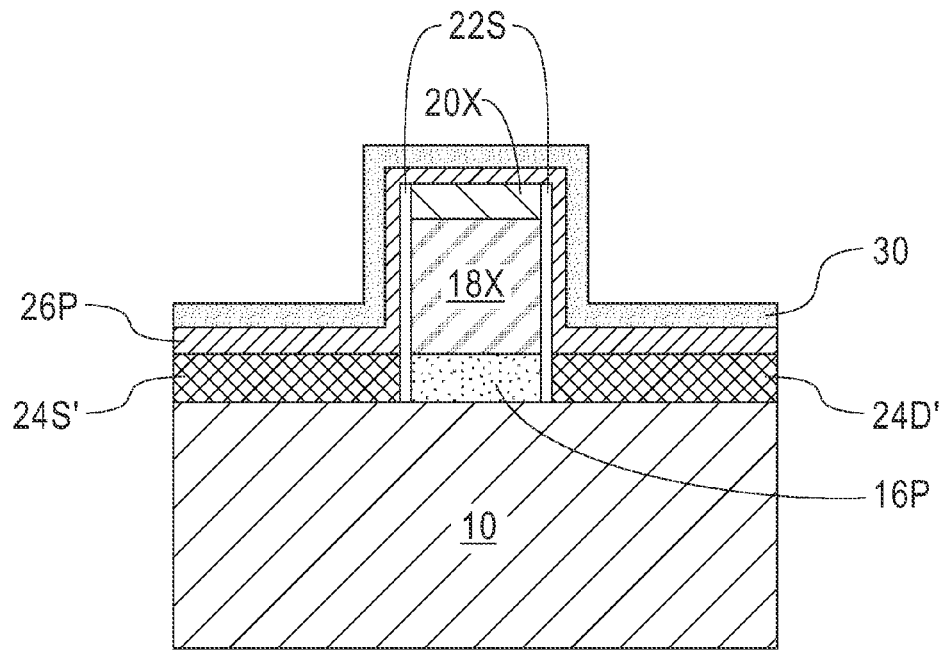
FIG. 13C is a cross sectional view of the exemplary semiconductor structure of FIG. 13A through vertical plane C-C'.
Figure 13D:
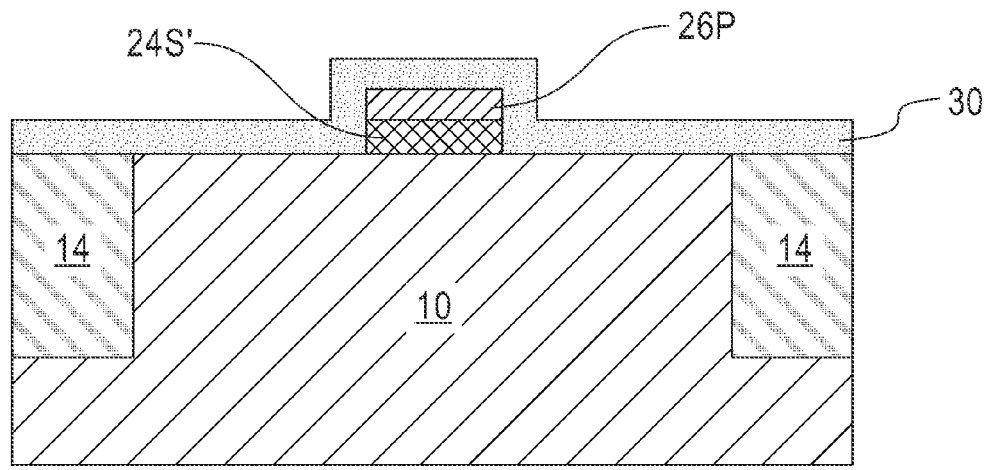
FIG. 13D is a cross sectional view of the exemplary semiconductor structure of FIG. 13A through vertical plane D-D'.
Figure 14A:
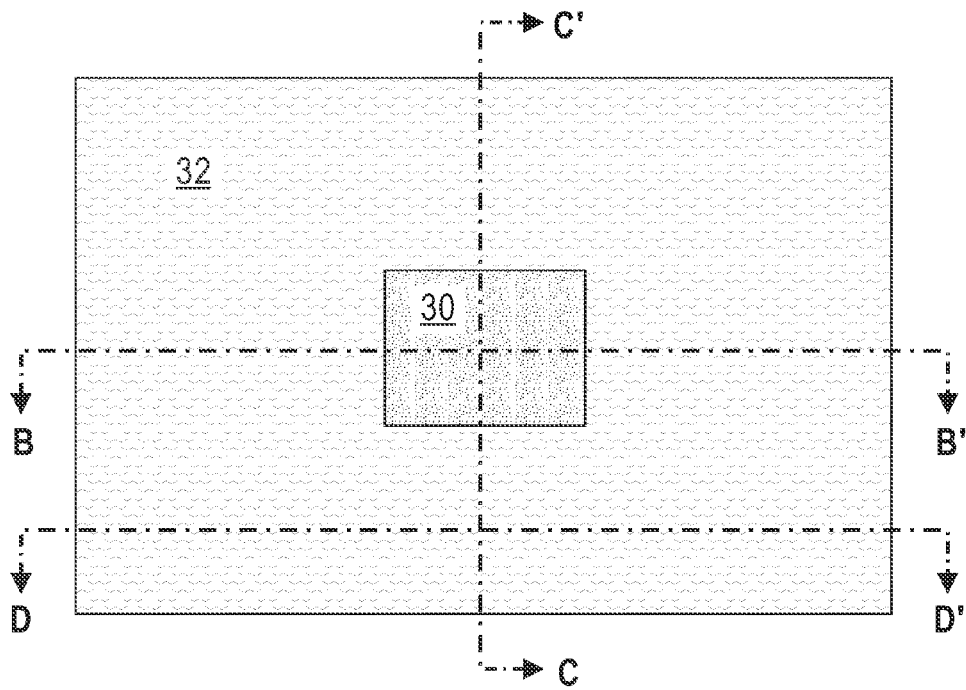
FIG. 14A is a top down view of the exemplary semiconductor structure of FIGS. 13A-13D after forming a non-stick nucleotide, DNA and DNA polymerase material structure.
Figure 14B:
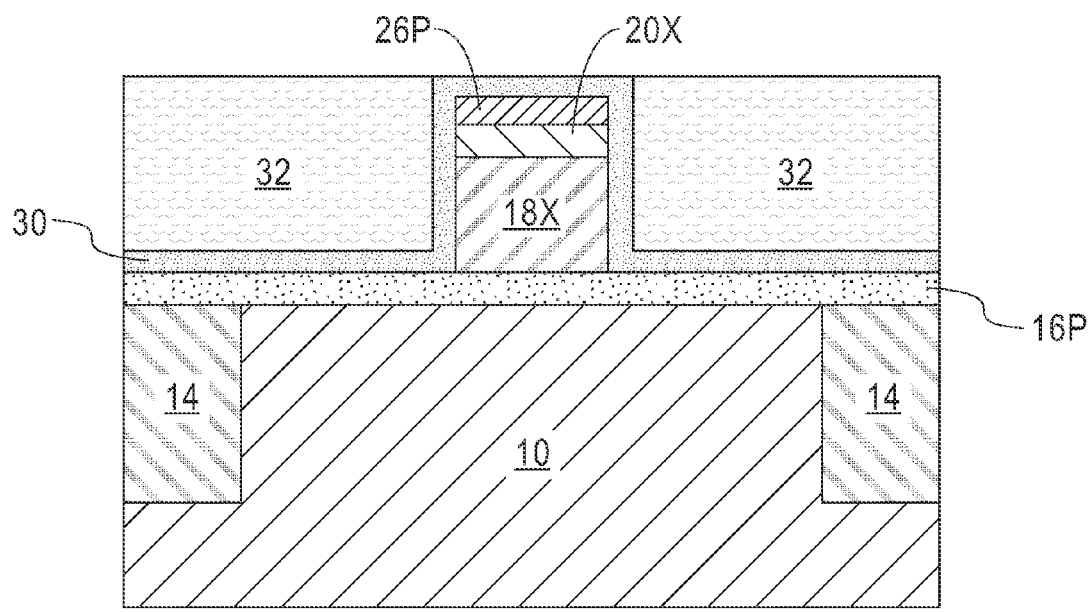
FIG. 14B is a cross sectional view of the exemplary semiconductor structure of FIG. 14A through vertical plane B-B'.
Figure 14C:
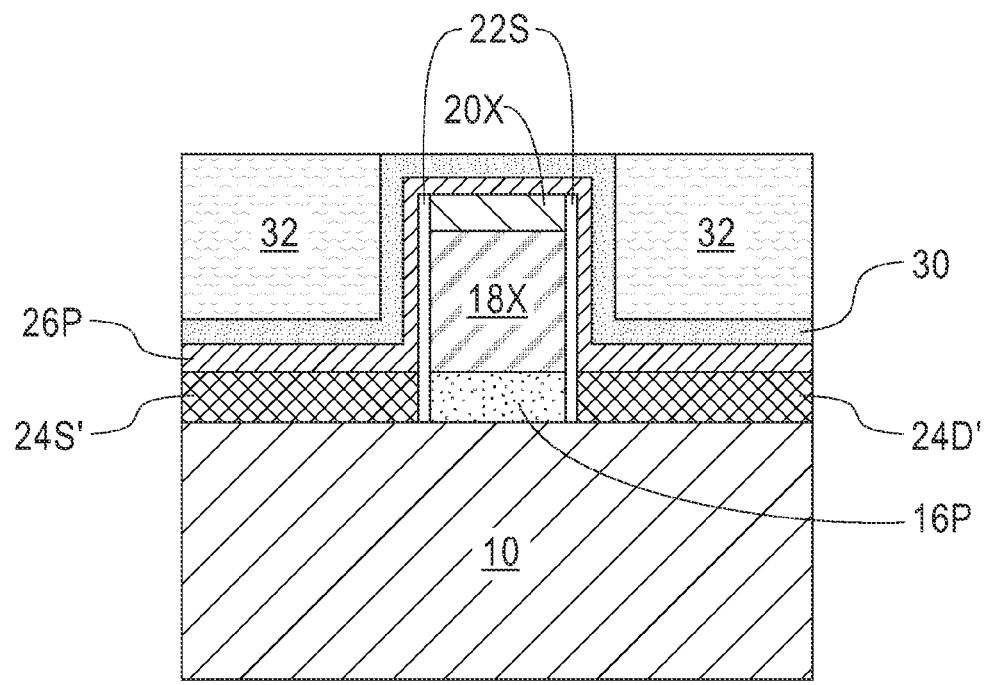
FIG. 14C is a cross sectional view of the exemplary semiconductor structure of FIG. 14A through vertical plane C-C'.
Figure 14D:
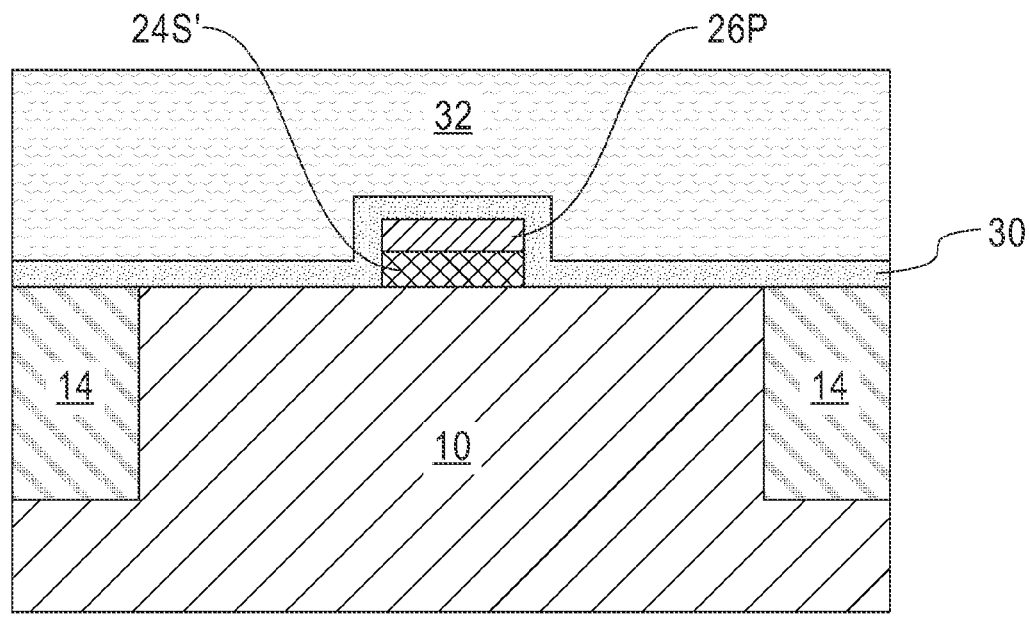
FIG. 14D is a cross sectional view of the exemplary semiconductor structure of FIG. 14A through vertical plane D-D'.
Figure 15A:
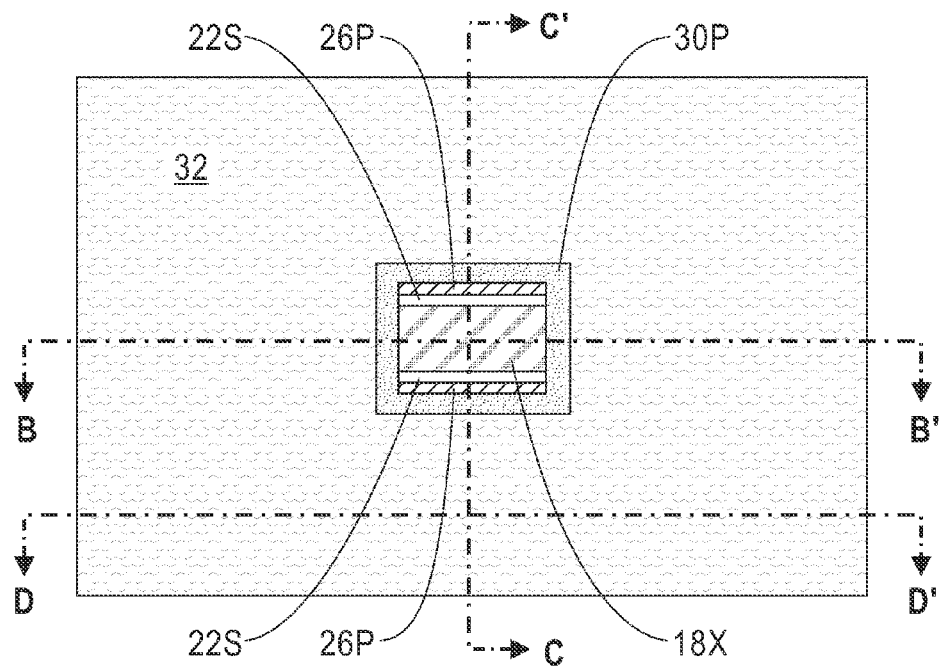
FIG. 15A is a top down view of the exemplary semiconductor structure of FIGS. 14A-14D after providing an opening that exposes a topmost surface of a remaining portion of the sacrificial gate layer that is formed after cutting the sacrificial gate structure.
Figure 15B:
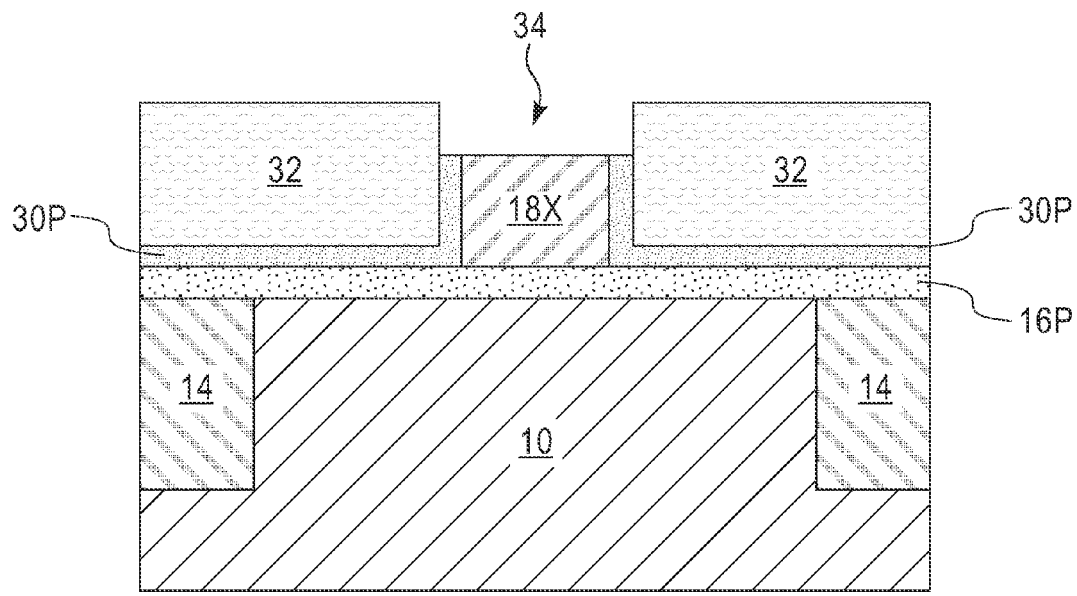
FIG. 15B is a cross sectional view of the exemplary semiconductor structure of FIG. 15A through vertical plane B-B'.
Figure 15C:
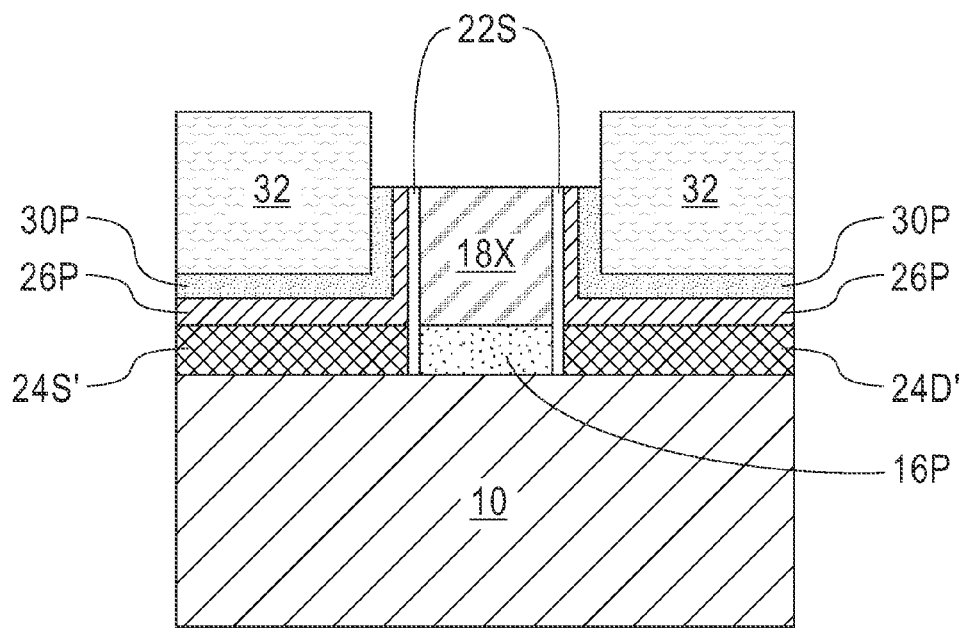
FIG. 15C is a cross sectional view of the exemplary semiconductor structure of FIG. 15A through vertical plane C-C'.
Figure 15D:
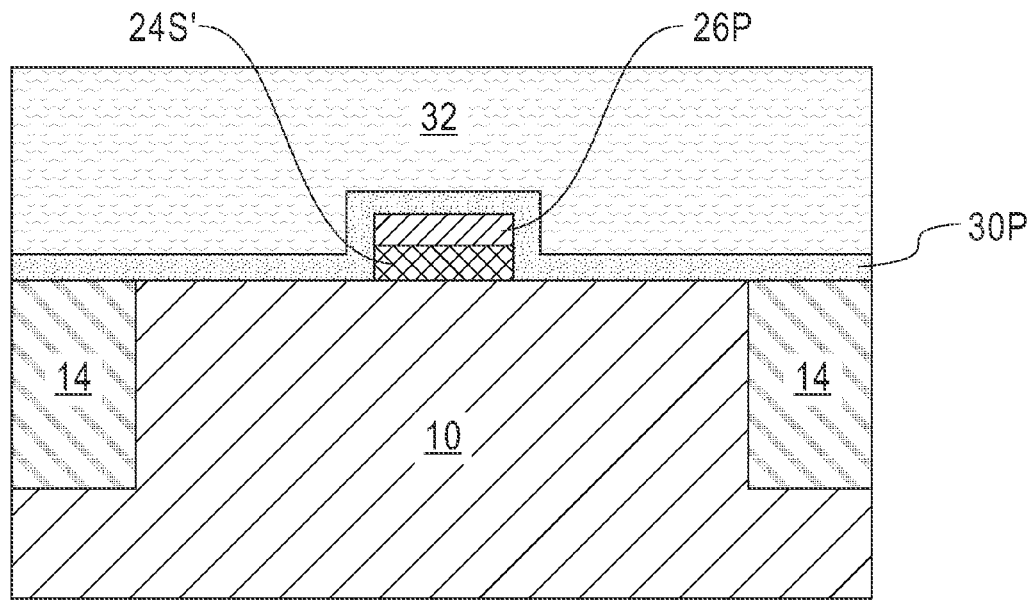
FIG. 15D is a cross sectional view of the exemplary semiconductor structure of FIG. 15A through vertical plane D-D'.

Referring now to FIGS. 4A-4D, there are illustrated various views of the exemplary semiconductor structure of FIGS. 3A-3B after patterning the sacrificial gate stack (18L, 20L) to provide a sacrificial gate structure (18P, 20P) and the underlying gate dielectric layer 16L to provide a gate dielectric portion 16P. The patterning of the sacrificial gate stack (18L, 20L) and the underlying gate dielectric layer 16L may comprise lithography and etching as mentioned above. In one embodiment, a single etching process may be used to provide the exemplary semiconductor structure shown in FIGS. 4A-4D. In another embodiment, two or more etching steps may be used to provide the exemplary semiconductor structure shown in FIGS. 4A-4D. As is shown in FIGS. 4B-4C, the sacrificial gate structure (18P, 20P) is located on a surface of the gate dielectric portion 16P. Also, and as shown in cross sectional views shown in FIGS. 4B-4C, sidewall surfaces of the sacrificial gate structure (18P, 20P) are vertical coincident, i.e., vertically aligned with, the sidewall surfaces of the gate dielectric portion 16P.

Referring now to FIGS. 5A-5D, there are illustrated various views of the exemplary semiconductor structure of FIGS. 4A-4D after forming a spacer dielectric material layer 22. The spacer dielectric material layer 22 is formed over the exposed surfaces (sidewall and topmost) of the sacrificial gate structure (18P, 20P), exposed sidewall surfaces of the gate dielectric portion 16P, and on the exposed topmost surface of the semiconductor substrate 10 and the adjacent trench isolation structure 14. The spacer dielectric material layer 22 may comprise a spacer dielectric material such as, for example, silicon dioxide and/or silicon nitride. The spacer dielectric material layer 22 can be formed utilizing any well known deposition process such as, for example, chemical vapor deposition (CVD), plasma enhanced chemical vapor deposition (PECVD) or physical vapor deposition. The spacer dielectric material layer 22 can have a thickness from 5 nm to 20 nm. Other thicknesses that are lesser than, or greater than, the aforementioned thickness range can also be employed as the thickness of the spacer dielectric material layer 22.

Referring now to FIGS. 6A-6D, there are illustrated various views of the exemplary semiconductor structure of FIGS. 5A-5D after patterning the spacer dielectric material layer 22 into a dielectric spacer 22S which is located on sidewall surfaces of the sacrificial gate structure (18P, 20P) and the gate dielectric portion 16P. The patterning of the spacer dielectric material layer 22 may include a spacer etch such as, for example, reactive ion etching. In some embodiments of the present application and as illustrated, the dielectric spacer 22S may have a topmost surface that is coplanar with a topmost surface of the sacrificial gate structure (18P, 20P), e.g., a topmost surface of the sacrificial gate gap portion 20P. In yet other embodiments, the topmost surface of the dielectric spacer 22S may be slightly offset (e.g., 1 nm to 3 nm) from a topmost surface of the sacrificial gate structure (18P, 20P).

Referring now to FIGS. 7A-7D, there are illustrated various views of the exemplary semiconductor structure of FIGS. 6A-6D after forming a doped epitaxial source semiconductor material 24S on a first side of the sacrificial gate structure (18P, 20P) and a doped epitaxial drain semiconductor material 24D on a second side of the sacrificial gate structure (18P, 20P), the second side is opposite the first side.

The doped epitaxial source semiconductor material 24S and the doped epitaxial drain semiconductor material 24D may be formed utilizing an epitaxial growth (or deposition) process. In some embodiments a selective epitaxial growth (or deposition) process can be used to provide the doped epitaxial source and drain semiconductor material (24S, 24D); the term "selective" when used in conjugation with the phrase "selective epitaxial growth" denotes that the epitaxial material is grown only on semiconductor material surfaces not insulator or conductor surfaces. The terms "epitaxial growth and/or deposition" and "epitaxially formed and/or grown" mean the growth of a semiconductor material on a deposition surface of a semiconductor material, in which the semiconductor material being grown has the same crystalline characteristics as the semiconductor material of the deposition surface. In an epitaxial deposition process, the chemical reactants provided by the source gases are controlled and the system parameters are set so that the depositing atoms arrive at the deposition surface of the semiconductor substrate with sufficient energy to move around on the surface and orient themselves to the crystal arrangement of the atoms of the deposition surface. Therefore, an epitaxial semiconductor material has the same crystalline characteristics as the deposition surface on which it is formed. For example, an epitaxial semiconductor material deposited on a {100} crystal surface will take on a {100} orientation. In the present application, the doped epitaxial source and drain semiconductor materials (24S, 24D) have an epitaxial relationship with the underlying semiconductor substrate 10.

Examples of various epitaxial growth process apparatuses that are suitable for use in forming the doped epitaxial source and drain semiconductor material (24S, 24D) include, e.g., rapid thermal chemical vapor deposition (RTCVD), low-energy plasma deposition (LEPD), ultra-high vacuum chemical vapor deposition (UHVCVD), atmospheric pressure chemical vapor deposition (APCVD) and molecular beam epitaxy (MBE). The temperature for epitaxial deposition typically ranges from 550° C. to 900° C. Although higher temperature typically results in faster deposition, the faster deposition may result in crystal defects and film cracking.

A number of different sources may be used for the deposition of the doped epitaxial source and drain semiconductor material 24S, 24D. In some embodiments, the source gas for the deposition of the doped epitaxial source and drain semiconductor material (24S, 24D) includes a silicon containing gas source. Examples of silicon gas sources include silane, disilane, trisilane, tetrasilane, hexachlorodisilane, tetrachlorosilane, dichlorosilane, trichlorosilane, methylsilane, dimethylsilane, ethylsilane, methyldisilane, dimethyldisilane, hexamethyldisilane and combinations thereof. In another embodiment, the source gas for the deposition of the doped epitaxial source and drain semiconductor material (24S, 24D) may include a germanium containing source gas. Examples of germanium containing source gases include germane, digermane, halogermane, dichorogermane, trichlorogermane, tetrachlorogemane and combinations thereof. In some embodiments, a silicon containing gas source and a germanium containing gas source can be used in conjunction to provide the doped epitaxial source and drain semiconductor material (24S, 24D). Carrier gases like hydrogen, nitrogen, helium and argon can be used.

The dopant within the doped epitaxial source and drain semiconductor material (24S, 24D) may be a p-type dopant or an n-type dopant as mentioned above. In one embodiment of the present application, the dopant can be added during the epitaxial growth process. In another embodiment, the dopant can be added after epitaxially growing an intrinsic epitaxial semiconductor material by utilizing one of ion implantation or gas phase doping. A thermal anneal may follow the introduction of dopant within the intrinsic semiconductor material. The concentration of dopant that is presence within the doped epitaxial source and drain semiconductor material (24S, 24D) is within ranges typically used in forming metal oxide semiconductor field effect transistors (MOSFETs).

The doped epitaxial source and drain semiconductor materials (24S, 24D) have a topmost surface that is located beneath a topmost surface of the sacrificial gate structure (18P, 20P) and beneath a topmost surface of the dielectric spacer 22S. As is shown in the cross sectional shown in FIG. 7C, a sidewall surface of the doped epitaxial source and drain semiconductor material (24S, 24D) directly contacts a lower sidewall surface of the dielectric spacer 22S.

In some embodiments of the present application, source/drain regions can be formed by introducing ions via ion implantation into the exposed portion of the semiconductor substrate 10. The source/drain regions can be used alone or in conjunction with the doped epitaxial source and drain semiconductor materials (24S, 24D) mentioned above.

Referring now to FIGS. 8A-8D, there are illustrated various views of the exemplary semiconductor structure of FIGS. 7A-7D after forming a hard mask layer 26. The hard mask layer 26 may include one of the hard mask materials mentioned above in providing the hard mask portion 12. The hard mask layer 26 may also be formed utilizing one of the deposition process mentioned above in providing the hard mask portion 12. The hard mask layer 26 may have a thickness from 20 nm to 50 nm, although other thicknesses that are lesser than or greater than the aforementioned thickness range can also be used as the thickness of the hard mask layer 26. As is shown, the hard mask layer 26 covers the exposed surfaces of the exemplary semiconductor structure shown in FIGS. 7A-7D including the exposed sidewalls of the dielectric spacer 22S, a topmost surface of the sacrificial gate structure (18P, 20P), and the topmost surface of the doped epitaxial source and drain semiconductor materials 24S, 24D.

Referring now to FIGS. 9A-9D, there are illustrated various views of the exemplary semiconductor structure of FIGS. 8A-8D after forming a sacrificial gate cut mask 28 on a surface of the hard mask layer 26. The sacrificial gate cut mask 28 may include a material stack of, from bottom to top, an optical planarization layer (OPL), an antireflective coating (ARC) and a photoresist material. In some embodiments, the OPL and/or the ARC may be omitted.

The OPL may include a self-planarizing material. In one example, the OPL can be an organic material including C, O, and H, and optionally including Si and/or F. In another example, the OPL can be amorphous carbon. The self-planarizing material that can provide the OPL can be formed by spin-on coating, chemical vapor deposition; plasma enhanced chemical vapor deposition, evaporation or chemical solution deposition. The thickness of the OPL can be from 10 nm to 300 nm, although lesser and greater thicknesses can also be employed.

The anti-reflective coating (ARC) includes any antireflective coating material that can reduce image distortions associated with reflections off the surface of underlying structure. In one example, the ARC comprises a silicon (Si)-containing antireflective coating material. The antireflective coating material that provides the ARC can be formed by spin-on coating, chemical vapor deposition; plasma enhanced chemical vapor deposition, evaporation or chemical solution deposition. The thickness of the ARC can be from 10 nm to 150 nm, although lesser and greater thicknesses can also be employed.

The photoresist material may include one of the previously mentioned photoresist materials that can be formed as described above. The material stack is then patterned to provide the sacrificial gate cut mask 28. As is shown in FIGS. 9A-9D, the sacrificial gate cut mask 28 lies perpendicular to the sacrificial gate structure (18P, 20P). A first portion of the sacrificial gate cut mask 28 is present atop a portion of the sacrificial gate structure (18P, 20P). Other portions of the sacrificial gate cut mask 28 are present atop the doped epitaxial source and drain semiconductor materials (24S, 24D).

Referring now to FIGS. 10A-10D, there are illustrated various views of the exemplary semiconductor structure of FIGS. 9A-9D after patterning the hard mask layer 26 utilizing the sacrificial gate cut mask 28 as an etch mask, and removing the sacrificial gate cut mask 28. The remaining hard mask layer 26 is referred to herein as a hard mask portion 26P. Hard mask portion 26P has the pattern of the sacrificial gate cut mask 28 mentioned above. The patterning of the hard mask layer can be performed utilizing an anisotropic etching process such as, for example, reactive ion etching. After performing the anisotropic etch, the sacrificial gate cut mask 28 can be removed utilizing a conventional cut mask removal process including, for example, ashing.

Referring now to FIGS. 11A-11D, there are illustrated various views of the exemplary semiconductor structure of FIGS. 10A-10D after cutting the sacrificial gate structure (18P, 20P) utilizing the remaining hard mask layer 26 (i.e., the hard mask portion 26P) as an etch mask. The cutting of the sacrificial gate structure (18P, 20P) can be performed utilizing an anisotropic etching process such as, for example, reactive ion. In this step of the present application, portions of the sacrificial gate structure (18P, 20P) that are not covered by the hard mask portion 26P are removed. The remaining sacrificial gate structure now includes a remaining portion of the sacrificial gate portion 18P and a remaining portion of the sacrificial gate cap portion 20P. The remaining sacrificial gate portion is now referred to a sacrificial gate cut portion 18X, while the remaining sacrificial gate cap portion is now referred to as a sacrificial gate cap cut portion 20X.

Referring now to FIGS. 12A-12D, there are illustrated various views of the exemplary semiconductor structure of FIGS. 11A-11D after removing exposed portions of the doped epitaxial source and drain semiconductor materials (24S, 24D). The exposed portions of the doped epitaxial source and drain semiconductor materials (24S, 24D) can be removed utilizing an etching process that is selective in removing the semiconductor material that provides the doped epitaxial source and drain semiconductor materials (24S, 24D). Portions of the doped epitaxial source and drain semiconductor materials (24S, 24D) remain in the exemplary semiconductor structure beneath the hard mask portion 26P. The remaining doped epitaxial source and drain semiconductor materials (24S, 24D) are now referred to as doped epitaxial source and drain semiconductor material structures (24S', 24D').

Referring now to FIGS. 13A-13D, there are illustrated various views of the exemplary semiconductor structure of FIGS. 12A-12D after forming a dielectric material liner 30. The dielectric material liner 30 that can be employed in the present application may include one of the dielectric materials mentioned above for the gate dielectric layer 16L. In one embodiment of the present application, the dielectric material liner 30 is composed of $Al_2O_3$. The dielectric material liner 30 may be formed utilizing one of the deposition processes mentioned above in forming the gate dielectric layer 16L. The dielectric material liner 30 can have a thickness in a range from 1 nm to 10 nm. Other thicknesses that are lesser than, or greater than, the aforementioned thickness range can also be employed for the dielectric material liner 30. As is shown, the dielectric material liner 30 covers the entirety of the exemplary semiconductor structure shown in FIGS. 12A-12B.

Referring now to FIGS. 14A-14D, there are illustrated various views of the exemplary semiconductor structure of FIGS. 13A-13D after forming a non-stick nucleotide, DNA and DNA polymerase material structure 32. The term "non-stick nucleotide, DNA and DNA polymerase material structure" denotes any material in which nucleotides, DNA and DNA polymerase do not adhere to; instead the nucleotides, DNA and DNA polymerase adhere to the gate dielectric portion 16P. The non-stick nucleotide, DNA and DNA polymerase material structure 32 is located on each side of the cut sacrificial gate structure (20X, 18X) and has a topmost surface that is coplanar with a topmost surface of the dielectric material liner 30 that is present atop the cut sacrificial gate structure (20X, 18X). The non-stick nucleotide, DNA and DNA polymerase material structure 32 may include any conductive metal or metal alloy. In one embodiment of the present application, the non-stick nucleotide, DNA and DNA polymerase material structure 32 can be composed of a metal such as, for example, aluminum.

The non-stick nucleotide, DNA and DNA polymerase material structure 32 can be formed by first depositing a layer of a conductive metal or metal alloy. After deposition of the layer of conductive metal or metal alloy, the layer of conductive metal or metal alloy is then subjected to a planarization process such as, for example, chemical mechanical polishing.

Referring now to FIGS. 15A-15D, there are illustrated various views of the exemplary semiconductor structure of FIGS. 14A-14D after providing an opening 34 that exposes a topmost surface of a remaining portion of the sacrificial gate layer (i.e., the sacrificial gate cut portion 18X) that is formed after cutting the sacrificial gate structure. The opening 34 is provided by utilizing one or more etching steps which stops on the topmost surface of the sacrificial gate cut portion 18X. Notably, the exposed portions of the dielectric material liner 30, the sacrificial gate cap cut portion 20X, and an upper portion of the dielectric spacer 22S are removed utilizing one or more etching steps. The remaining portions of the dielectric material liner 30 can now be referred to herein as a dielectric material liner portion 30P. In one embodiment, the one or more etching steps include one or more reactive ion etching steps.

Referring now to FIGS. 16A-16D, there are illustrated various views of the exemplary semiconductor structure of FIGS. 15A-15D after removing the exposed portion of the remaining portion of the sacrificial gate layer (i.e., the sacrificial gate cut portion 18X) within the opening 34. A cavity 36 is formed within the non-stick nucleotide, DNA and DNA polymerase material structure 32 that exposes a portion of a topmost surface of the gate dielectric portion 16P. The removal of the sacrificial gate cut portion 18X is performed utilizing an etching process that is selective in removing the sacrificial gate material that provides the sacrificial gate layer 18L. In one embodiment of the present application and when the sacrificial gate cut portion 18X includes amorphous silicon, either wet-etch (such as, for example, TMAH (i.e., tetramethylammonium hydroxide), KOH (i.e., potassium hydroxide) or $NH_4OH$ (i.e., ammonium hydroxide) or dry etch (such as, for example, RIE (i.e., reactive ion etching) or ICP (i.e., inductively coupled plasma) can be used to remove the sacrificial gate cut portion 18X. As is shown, cavity 36 has a upper portion of a first width, w1, and a lower portion of a second width, w2, that is less than the first width. In one embodiment, the second width of cavity 36 is from 10 nm to 150 nm.

The cavity 36 may have a shape, as seen from a top down view, that can be square, rectangular circular or hexagonal. The cavity 36 may have a shape, as seen from a cross sectional view, that is U-shaped, trapezoidal or reverse trapezoidal.

Figure 16A:
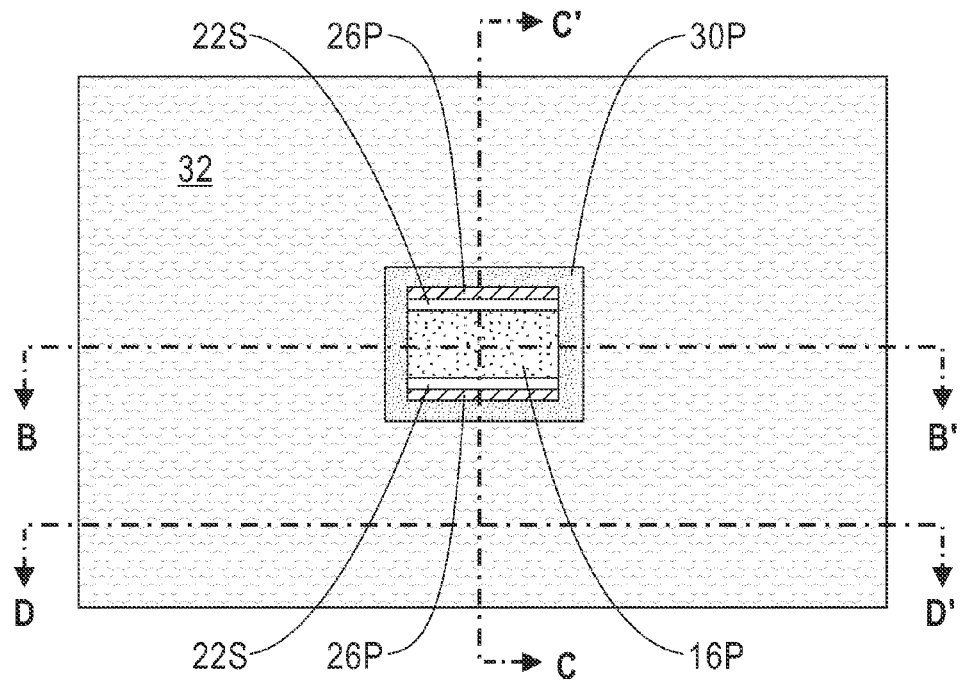
FIG. 16A is a top down view of the exemplary semiconductor structure of FIGS. 15A-15D after removing the remaining portion of the sacrificial gate layer within the opening.
Figure 16B:
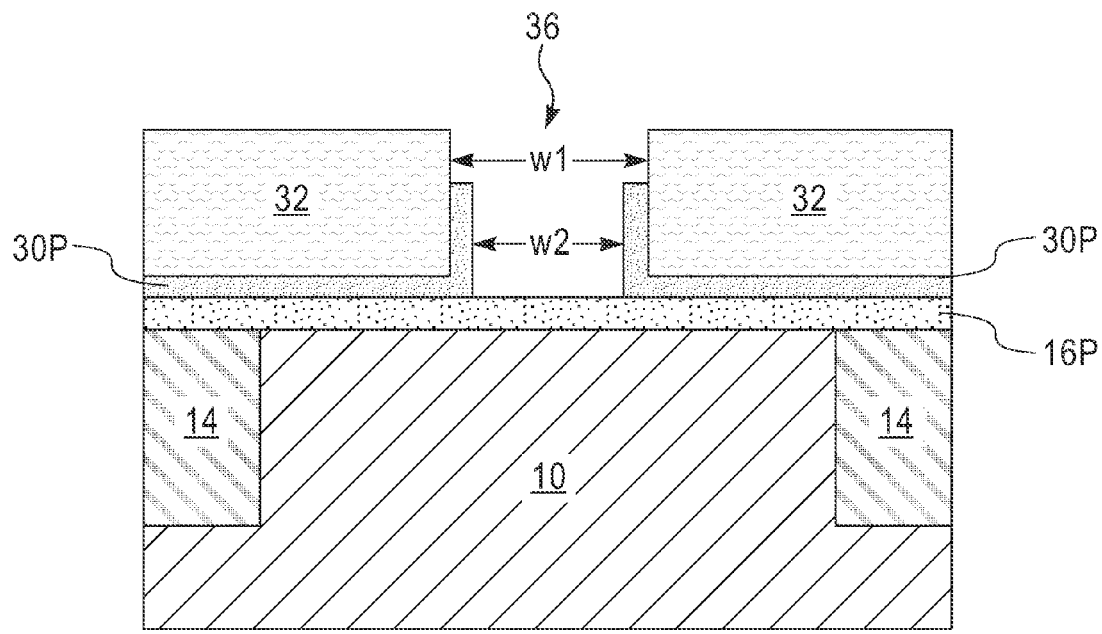
FIG. 16B is a cross sectional view of the exemplary semiconductor structure of FIG. 16A through vertical plane B-B'.
Figure 16C:
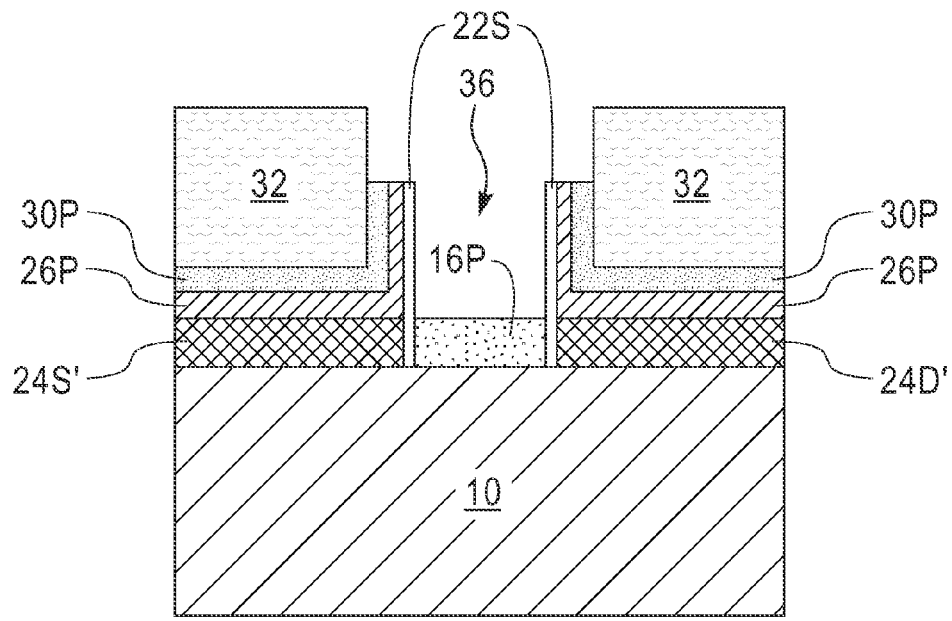
FIG. 16C is a cross sectional view of the exemplary semiconductor structure of FIG. 16A through vertical plane C-C'.
Figure 16D:
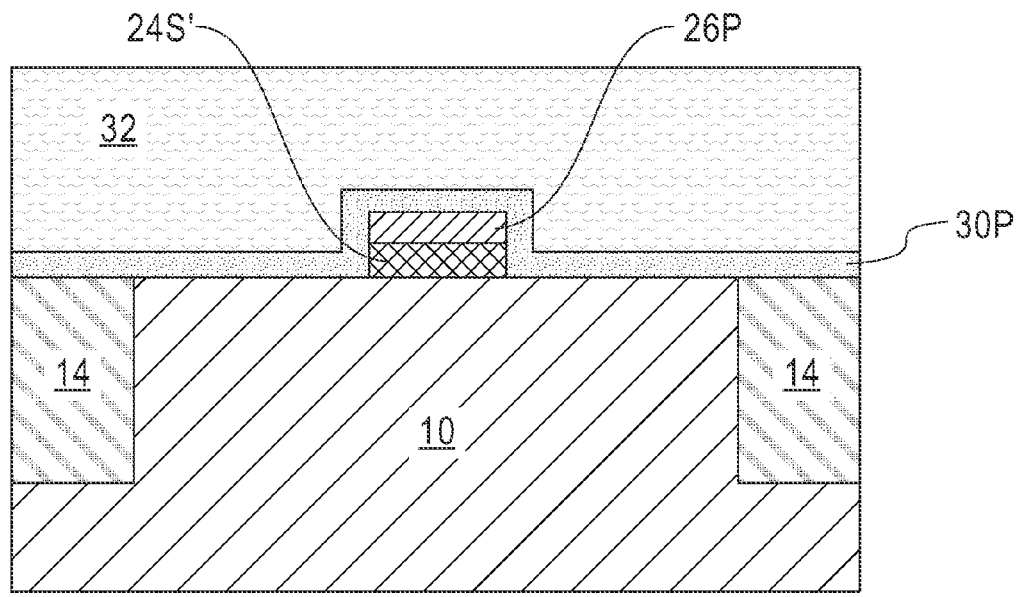
FIG. 16D is a cross sectional view of the exemplary semiconductor structure of FIG. 16A through vertical plane D-D'.

Notably, FIGS. 16A-16B illustrates a semiconductor structure that can be used for DNA sequencing detection. The semiconductor structure includes a doped epitaxial source semiconductor material structure 24S' located on a first portion of a semiconductor substrate 10 and a doped epitaxial drain semiconductor material structure 24D' located on a second portion of the semiconductor substrate 10. A gate dielectric portion 16P is located on a third portion of the semiconductor substrate 10 and positioned between the doped epitaxial source semiconductor material structure 24S' and the doped epitaxial drain semiconductor material structure 24D'. A non-stick nucleotide, DNA and DNA polymerase material structure 32 is located atop the doped epitaxial source semiconductor material structure 24S' and atop the doped epitaxial drain semiconductor material structure 24D', wherein a cavity 36 is present in the non-stick nucleotide, DNA and DNA polymerase material structure 32 that exposes a topmost surface of the gate dielectric portion 16P. In the drawings, element 10C represents a semiconductor channel region of the semiconductor structure that is located between the doped epitaxial source and drain semiconductor material structure (24S', 24D').

Figure 17A:
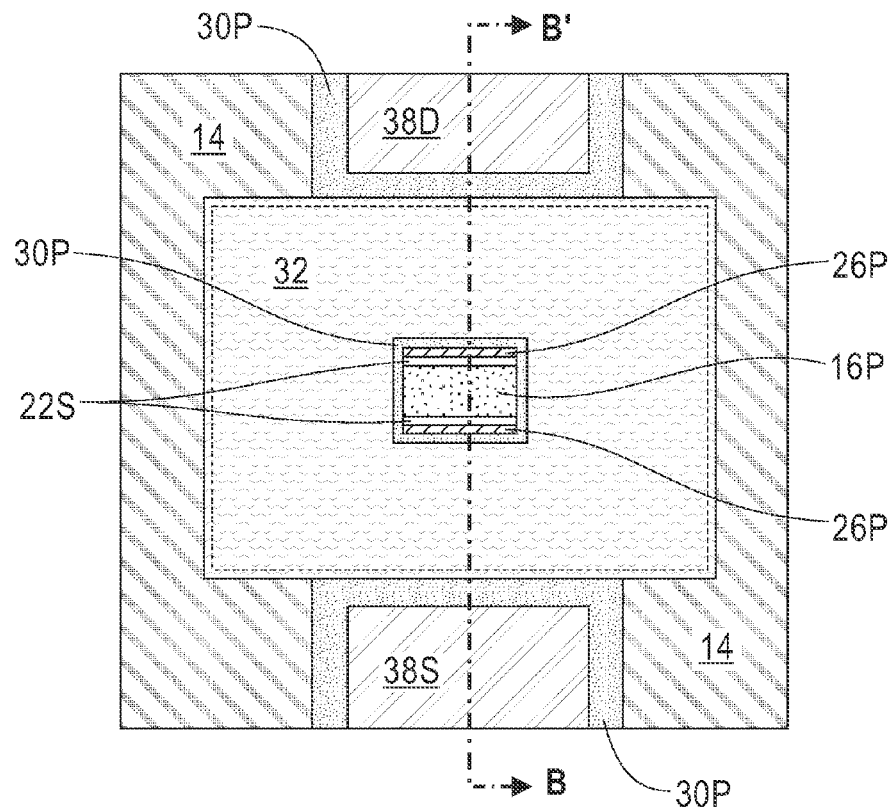
FIG. 17A is a top down view of the exemplary semiconductor structure of FIGS. 16A-16D after forming a source-side metal contact structure and a drain-side metal contact structure.
Figure 17B:
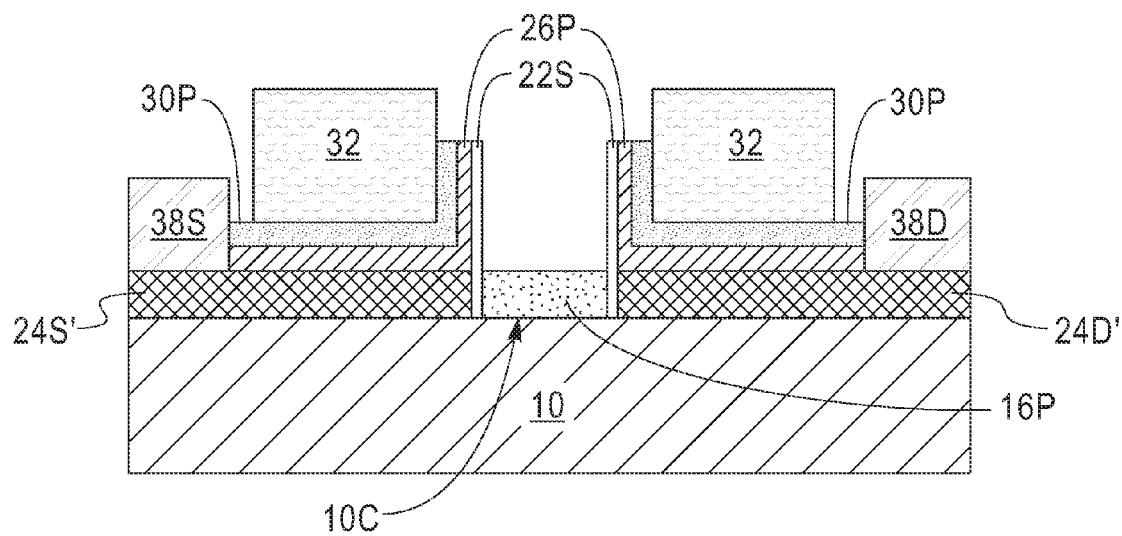
FIG. 17B is a cross sectional view of the exemplary semiconductor structure of FIG. 17A through vertical plane B-B'.

Referring now to FIGS. FIGS. 17A-17B, there are illustrated various views of the exemplary semiconductor structure of FIGS. 16A-16D after forming a source-side metal contact structure 38S and a drain-side metal contact structure 38D. As is shown, the source-side metal contact structure 38S has a bottommost surface that directly contact a topmost surface of the doped epitaxial source material structure 24S', while the drain-side metal contact structure 38D has a bottommost surface that directly contact a topmost surface of the doped epitaxial drain material structure 24D'. The source-side metal contact structure 38S and drain-side metal contact structure 38D can be formed by first providing a contact opening (not shown) to expose a topmost surface of the doped epitaxial source and drain material structures (24S', 24D'). The contact opening can be formed by lithography and etching. Once the contact opening is provided, a conductive metal or metal alloy is deposited and thereafter the deposited conductive metal of metal alloy is patterned by lithography and etching so as to provide the source-side metal contact structure 38S and drain-side metal contact structure 38D. In one example, the source-side metal contact structure 38S and drain-side metal contact structure 38D each include Cu, Al, W, Ni, or Pt. As is shown, the source-side metal contact structure 38S and drain-side metal contact structure 38D do not physical contact any portion of the non-stick nucleotide, DNA and DNA polymerase material structure 32.

Figure 18:
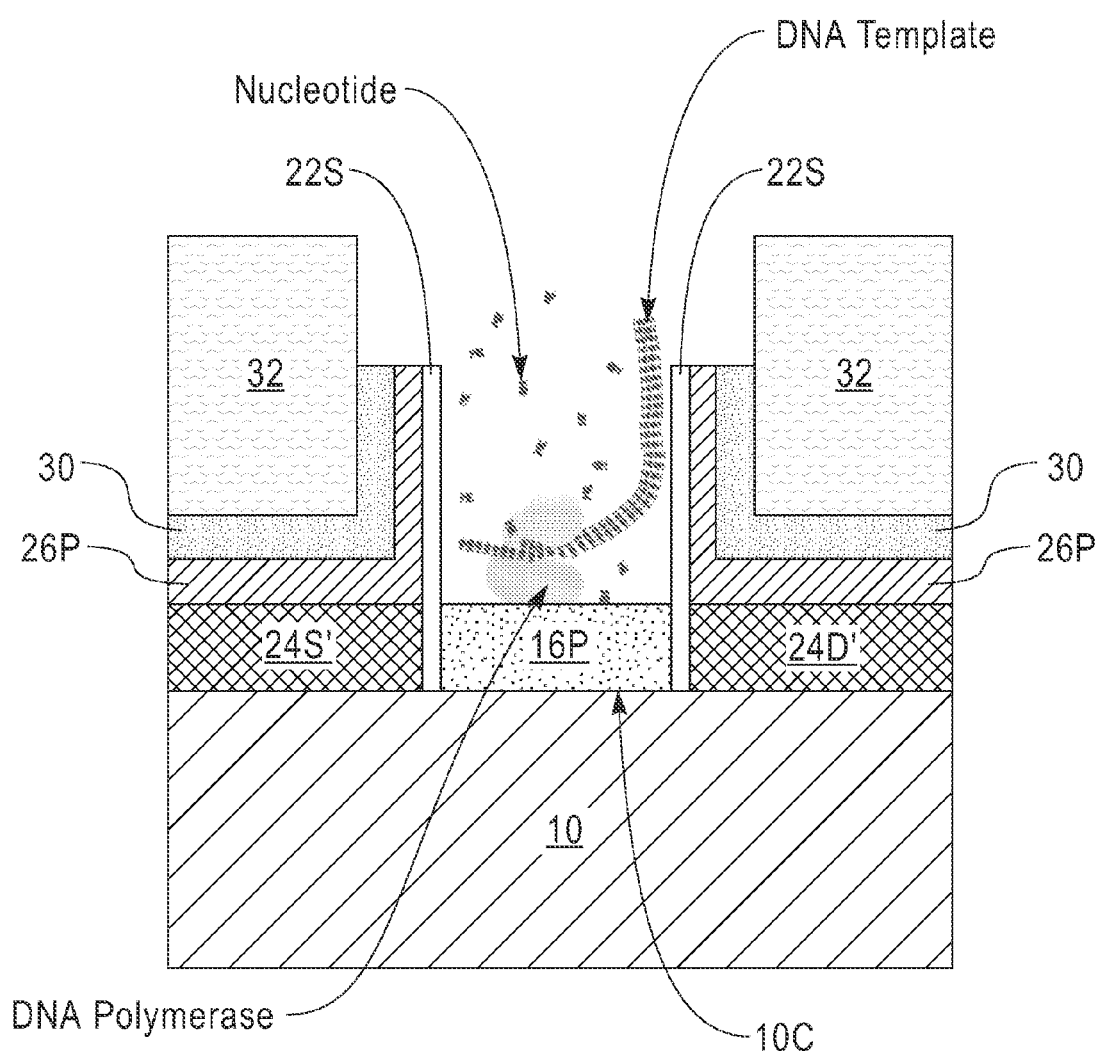
FIG. 18 is a cross sectional view of the exemplary semiconductor structure of FIGS. 17A-17B as employed for DNA sequencing detection.

Referring now to FIG. 18, there is illustrated the exemplary semiconductor structure of FIGS. FIGS. 17A-17B as employed for DNA sequencing detection. In accordance with an embodiment of the present application, a DNA polymerase is formed within the cavity 36. By "DNA polymerase" it is meant any enzyme that can create DNA molecules assembling nucleotides that are the basic building blocks of DNA. These enzymes are essential to DNA replication and usually work in pairs to create two identical DNA strands from a single original DNA molecule. Examples of such DNA polymerase that can be employed in the present application include Prokaryotic or Eukaryotic DNA polymerases. In one embodiment, Prokaryotic Family A polymerases can be used.

The DNA polymerase can be formed within the cavity 36 utilizing techniques well known to those skilled in the art. In one example, the DNA polymerase can be formed utilizing an immobilization process.

A DNA template is then attached to a surface of the DNA polymerase in accordance with an embodiment of the present application. By "DNA template" it is meant any single strand of DNA on which a new strand of DNA are made following the complementary base pairing rules. A primer can also be attached to the DNA to enable the starting process of the DNA replication. The DNA template with primer is provided in a solution that also contains various nucleotides. By "nucleotides" it is meant organic molecules that serve as the monomers, or subunits, of nucleic acids, like DNA and RNA. The building blocks of nucleic acids, nucleotides are composed of a nitrogenous base (i.e., one of adenine (A), guanine (G), thymine (T) and cytosine (C)), a five-carbon sugar (ribose or deoxyribose), and at least one phosphate group.

Whenever the DNA template reacts with one of the 4 different types of the nucleotides sequentially, the charge on the gate will vary depending upon the type of the nucleotide which provides a change in the threshold voltage, which in turn provides a change in drain current that can be measured utilizing the FET device of the present application.

In accordance with the present application, the solution containing the DNA template is added utilizing techniques that are well known to those skilled in the art. For example, the solution containing the DNA template can be added by drop wise addition from a dropper or pipette. After addition of the above mentioned solution, the DNA template becomes attached to the DNA polymerase. The nucleotides then attach to the DNA template according to sequence.

In accordance with an embodiment of the present application, the DNA template and DNA polymerase (or any other conductive material) which contacts the gate dielectric portion 16P can act as the gate of the device and change channel potential whenever a reaction takes place.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A semiconductor structure comprising:
   a doped epitaxial source semiconductor material structure located on a first portion of a semiconductor substrate and a doped epitaxial drain semiconductor material structure located on a second portion of said semiconductor substrate;
   a gate dielectric portion located on a third portion of said semiconductor substrate and positioned entirely between, and spaced apart from, a sidewall edge of said doped epitaxial source semiconductor material structure and a sidewall edge of said doped epitaxial drain semiconductor material structure; and
   a non-stick nucleotide, DNA and DNA polymerase material structure located atop said doped epitaxial source semiconductor material structure and atop said doped epitaxial drain semiconductor material structure, wherein a cavity is present in said non-stick nucleotide, DNA and DNA polymerase material structure that exposes a topmost surface of said gate dielectric portion.

2. The semiconductor structure of claim 1, further comprising a DNA polymerase located on a portion of said topmost surface of said gate dielectric portion and within said cavity.

3. The semiconductor structure of claim 2, further comprising a DNA template attached to a surface of said DNA polymerase, wherein said DNA template is present in a solution that further contains various nucleotides.

4. The semiconductor structure of claim 1, further comprising a source-side metal contact structure located on a portion of a topmost surface of said doped epitaxial source semiconductor material structure and a drain-side metal contact structure located on a portion of a topmost surface of said doped epitaxial drain semiconductor material structure.

5. The semiconductor structure of claim 4, wherein said source-side metal contact structure and said drain-side metal contact structure are each spaced apart from said non-stick nucleotide, DNA and DNA polymerase material structure.

6. The semiconductor structure of claim 1, further comprising a dielectric material liner portion located on a bottommost surface and a sidewall surface of said non-stick nucleotide, DNA and DNA polymerase material structure.

7. The semiconductor structure of claim 6, further comprising a hard mask portion located directly beneath said dielectric material liner portion.

8. The semiconductor structure of claim 7, further comprising a dielectric spacer located on exposed sidewall surface of said hard mask portion, said dielectric spacer having a portion that separates said gate dielectric portion from said doped epitaxial source semiconductor material structure or said doped epitaxial drain semiconductor material structure.

9. The semiconductor structure of claim 1, wherein said cavity has an upper portion of a first width and a lower portion of a second width, wherein said second width is less than the first width.

10. The semiconductor structure of claim 9, wherein said second width is from 10 nm to 150 nm.

11. The semiconductor structure of claim 1, wherein said semiconductor substrate comprises silicon doped with a p-type dopant.

12. The semiconductor structure of claim 1, wherein said gate dielectric portion has a bottommost surface that is in direct physical contact with a topmost surface of said semiconductor substrate.

13. A semiconductor structure comprising:
a doped epitaxial source semiconductor material structure located on a first portion of a semiconductor substrate and a doped epitaxial drain semiconductor material structure located on a second portion of said semiconductor substrate;
a gate dielectric portion located on a third portion of said semiconductor substrate and positioned between said doped epitaxial source semiconductor material structure and said doped epitaxial drain semiconductor material structure;
a non-stick nucleotide, DNA and DNA polymerase material structure located atop said doped epitaxial source semiconductor material structure and atop said doped epitaxial drain semiconductor material structure, wherein a cavity is present in said non-stick nucleotide, DNA and DNA polymerase material structure that exposes a topmost surface of said gate dielectric portion;
a dielectric material liner portion located on a bottommost surface and a sidewall surface of said non-stick nucleotide, DNA and DNA polymerase material structure;
a hard mask portion located directly beneath said dielectric material liner portion; and
a dielectric spacer located on exposed sidewall surface of said hard mask portion, said dielectric spacer having a portion that separates said gate dielectric portion from said doped epitaxial source semiconductor material structure or said doped epitaxial drain semiconductor material structure.

14. The semiconductor structure of claim 13, further comprising a DNA polymerase located on a portion of said topmost surface of said gate dielectric portion and within said cavity.

15. The semiconductor structure of claim 14, further comprising a DNA template attached to a surface of said DNA polymerase, wherein said DNA template is present in a solution that further contains various nucleotides.

16. The semiconductor structure of claim 13, further comprising a source-side metal contact structure located on a portion of a topmost surface of said doped epitaxial source semiconductor material structure and a drain-side metal contact structure located on a portion of a topmost surface of said doped epitaxial drain semiconductor material structure.

17. The semiconductor structure of claim 16, wherein said source-side metal contact structure and said drain-side metal contact structure are each spaced apart from said non-stick nucleotide, DNA and DNA polymerase material structure.

18. The semiconductor structure of claim 13, wherein said cavity has an upper portion of a first width and a lower portion of a second width, wherein said second width is less than the first width.

* * * * *